US005656721A

United States Patent [19]
Albert et al.

[11] Patent Number: 5,656,721
[45] Date of Patent: Aug. 12, 1997

[54] PEPTIDE DERIVATIVES

[75] Inventors: Rainer Albert, Basel; Wilfried Bauer, Lampenberg; Francois Cardinaux, Seewen; Monika Mergler, Liestal; Janos Pless, Basel; Walter Prikoszovich, Allschwil, all of Switzerland

[73] Assignee: Sandoz Ltd., Basel, Switzerland

[21] Appl. No.: 272,704

[22] Filed: Jul. 7, 1994

Related U.S. Application Data

[62] Division of Ser. No. 138,567, Oct. 18, 1993, abandoned, which is a continuation of Ser. No. 782,021, Oct. 24, 1991, abandoned, which is a continuation of Ser. No. 108,188, Oct. 13, 1987, abandoned.

[30] Foreign Application Priority Data

| Oct. 13, 1986 | [DE] | Germany | 36 34 797.3 |
| Oct. 13, 1986 | [DE] | Germany | 36 34 826.0 |
| Oct. 13, 1986 | [DE] | Germany | 36 34 825.2 |
| Apr. 14, 1987 | [DE] | Germany | 37 12 626.1 |
| Aug. 17, 1987 | [CH] | Switzerland | 03153/87 |

[51] Int. Cl.$^6$ .................................................. A61K 38/31
[52] U.S. Cl. .................. 530/300; 525/328.2; 525/374; 525/379; 525/380; 530/311; 530/334
[58] Field of Search .................. 530/334, 300, 530/311

[56] References Cited

U.S. PATENT DOCUMENTS

| 4,254,023 | 3/1981 | Stewart et al. | 424/127 |
| 4,395,403 | 7/1983 | Low et al. | 530/330 |

FOREIGN PATENT DOCUMENTS

| 2548673 | 1/1983 | France. |
| 2206352 | 1/1989 | United Kingdom. |
| 8802756 | 1/1988 | WIPO. |

*Primary Examiner*—Bernard Lipman
*Attorney, Agent, or Firm*—Robert S. Honor; Melvyn M. Kassenoff; Thomas O. McGovern

[57] ABSTRACT

The present invention provides a sugar derivative of a biologically active peptide, which derivative has a prolonged duration of action when compared to the non-sugar modified peptide, and contains at least on one of the amino acid units a sugar residue which is attached to an amino group thereof by a coupling other than a direct N-glycosidic bond, and additionally, when it is a condensation product of a carboxyl group containing sugar and a peptide with less than 8 amino acid units, by a coupling other than a direct amide bond.

9 Claims, No Drawings

PEPTIDE DERIVATIVES

This is a division of application Ser. No. 08/138,567, filed Oct. 18, 1993, which in turn is a continuation of application Ser. No. 07/782,021, filed Oct. 24, 1991, which in turn is a continuation of application Ser. No. 07/108,188, filed Oct. 13, 1987, all of which are now abandoned.

The present invention relates to peptides, their production, pharmaceutical preparations containing them, and their use as medicaments.

The present invention provides a sugar derivative of a biologically active peptide, which derivative has a prolonged duration of action when Compared to the non-sugar modified peptide and contains at least on one of the amino acid units a sugar residue which is attached to an amino group thereof by a coupling other than a direct N-glycosidic bond, and additionally, when it is a condensation product of a carboxyl group containing sugar and a peptide with less than 8 amino acid units, by a coupling other than a direct amide bond.

Hereinafter these compounds are referred to as compounds of the invention.

By non-sugar modified peptide is meant the structurally corresponding peptide not having the sugar residue or residues. Hereinafter this is referred to as the unmodified peptide.

We have moreover found that the compounds of the invention show particularly interesting and surprising pharmacological properties, especially a longer duration of action, e.g. as described hereinafter.

We have found that incorporation of a sugar residue or residues, even when bound in a different manner to normal glycosylation e.g. of Asn or Ser, induces these properties.

It is preferred to introduce these sugar residues on amino groups of amino acids remote from the active site of the peptide.

The term peptides as used herein include: peptides (e.g. di-, tri-peptides), oligo-peptides, polypeptides, and proteins. Preferably the peptide is of more than 7 amino acid units. Conveniently the peptide is of 8 to 32 amino acid units. The term amino acid unit as used herein also includes an amino alcohol unit, e.g. a reduced amino acid.

The term biologically active peptides is used herein to cover in particular compounds having pharmacological or therapeutical activity, e.g. compounds which have hormonal, enzymatic or immunomodulatory activity, or which stimulate or inhibit such activity. These biologically active peptides encompass natural peptides isolated from nature or fermentation of cells, e.g. produced through genetic engineering, or synthesized and also their derivatives or analogues.

By derivatives and analogues is understood in particular natural peptides, wherein one or more amino acid units have been omitted and/or replaced by one or more other amino acid radical(s) and/or wherein one or more functional groups have been replaced by one or more other functional groups and/or wherein one or more groups have been replaced by one or several other isosteric groups. In general, the term covers all modified derivatives of a biologically active peptides, which exhibit a qualitatively similar effect to that of the unmodified peptide.

The sugars used may be e.g. any known mono- or oligosaccharide, especially a mono-, di- or triose or a derivative thereof, e.g. an amino- and/or carboxylic acid and/or reduced and/or esterified derivative thereof.

The sugar may be coupled e.g. to a N-terminal amino group and/or to at least one amino group of the peptide present in the side chain thereof.

The sugar may be coupled by one of its functional groups to the peptide either directly or indirectly by a bridging member e.g. an alkylene carbonyl group.

This coupling may be made in conventional manner, especially as hereinafter described.

In a preferred group of the compounds of the invention the sugar residue is attached to an amino group of the peptide by a coupling other than a direct N-glycosidic or direct amide bond.

A group of the compounds of the invention are preparable by an Amadori or Heyns rearrangement.

The invention also provides oral pharmaceutical preparations containing a compound of the invention especially those having at least 8 amino acids units.

The present invention provides in particular the following sugar derivatives of biologically active peptides of formula I a)

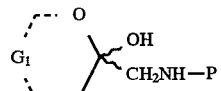

I wherein

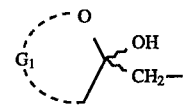

is the deoxy residue of a ketose, the residue being linked via the $CH_2$ group to the NH group of a biologically active peptide, and P is the residue of a biologically active peptide of formula $NH_2$—P, wherein the NH group is located on the N-terminal end or in a side chain of the peptide P, b) of formula II

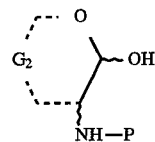

II wherein

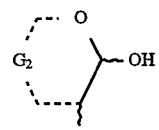

is the deoxy residue of an aldose, the radical being linked via the free bond to the NH group of a biologically active peptide, and P is the residue of a biologically active peptide of formula $NH_2$—P, wherein the NH group is located on the N-terminal end or in a side chain of the peptide P, c) of formula III

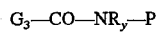

III wherein $G_3CO$ is the residue of a uronic acid, or of a polyhydroxymono- or di-carboxylic acid, $R_y$ is hydrogen, alkyl with 1 to 3 C-atoms or alkanol with 1 to 4 C-atoms, and P is the residue of a biologically active peptide of formula NH₂—P, containing at least 8 amino acid units wherein NR_y is located at the N-terminal end or in a side chain of the peptide P d) of formula IVa, IVb, IVc or IVd

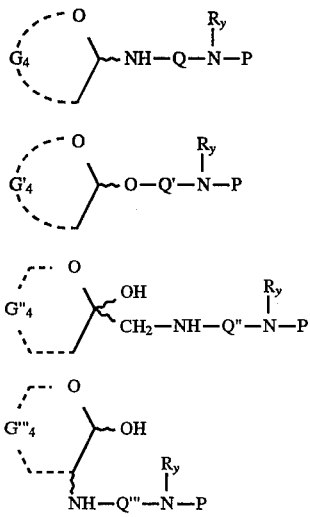

wherein P denotes the residue of a biologically active peptide of formula H₂N—P,

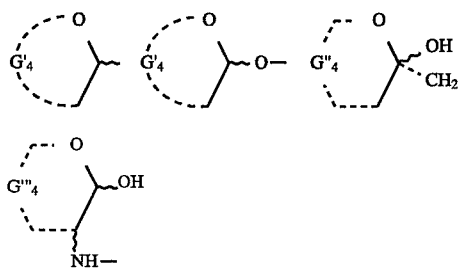

are sugar residues.

R_y is hydrogen, alkyl with 1 to 3 C-atoms or alkanoyl with 1 to 4 C-atoms, and Q, Q', Q" and Q'" are groups coupling the peptide residue with the sugar residue, wherein the NH group bonded to P is located at the N-terminal end or in a side chain of the peptide, or e) of formula Va or Vb HOH₂C—(CHOH)_c—CY—CH₂—NH—P    Va

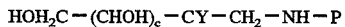
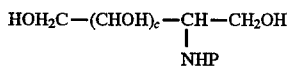

wherein
Y is H₂ or H, OH
c is 2 or 3 or 4
P is a residue of a biologically active peptide of formula H₂N—P wherein the NH group bonded to P is located at the N-terminal end or in a side chain of the peptide P, and any one of the free hydroxy groups in the polyol moiety of the compounds of formula V is optionally bound in glycosylic manner to a reducing mono-, di- or oligosaccharide or amino sugar,
as well as the acid addition salts and complexes of these polypeptide derivatives, with the provisos that a) in the above-mentioned compounds of formula I, P is other than a radical of a gastrin peptide with a C-terminal group ending in -Asp-Phe-NH₂, b) when in the compounds of formula IVb Q' is a phenyl-ring containing divalent radical or when in the compounds of formula IVd Q'" is the residue of an aliphatic dicarboxylic acid, then P—NH₂ is not a natural insulin, c) when in the compounds of formula III G₃—CO is the residue of an optionally N-acylated muramic acid then the second amino acid residue at the N-terminal end of the peptide P—NHR_y should not be the residue of an amino dicarboxylic acid.

A gastrin is a peptide which increases gastric acid secretion.

All the above-mentioned sugar residues may be mono-, di- or oligosaccharides. These sugars may contain heptoses, hexoses and/or pentoses, which may exist as pyranoses or furanoses.

In all the formulae I to V mentioned above only one sugar moiety per peptide residue has been shown. However, the invention also covers sugar derivatives of peptides having more than one free amino groups on the peptide residue, these derivatives containing e.g. 2,or 3 sugar residues per peptide residue.

The invention provides additionally all biologically active peptides which have more than one sugar residue which are linked as defined above.

The sugar polypeptides preferably contain 1 to 3 monosaccharide residues, which may be joined together as a disaccharide or tri-saccharide.

In all the above-mentioned compounds, the line ~ means that the bond may be in the α- or β-position.

In formula I

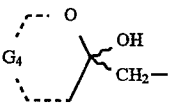

preferably is a) a residue of formula

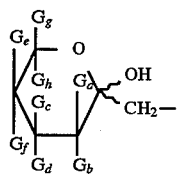

wherein one of radicals G_a and G_b is hydrogen and the other is OH, one of radicals G_c and G_d is hydrogen and the other is OH or O-glycosyl, wherein the glycosyl radical is derivable from a reducing mono-, di- or oligosaccharide, one of radicals G_e and G_f is hydrogen and the other is OH, one of radicals G_g and G_h is hydrogen and the other is hydrogen or CH₂OH e.g. wherein radicals G_a to G_h are selected such that the residue of formula VIa corresponds to a radical which is obtainable by means of an Amadori rearrangement from a natural or a synthetically accessible mono-, di- or oligosaccharide.

The following residues may be mentioned as examples of sugar residues of formula VIa:

Deoxyfructosyl, deoxytagatosyl, deoxysorbosyl, α-glucosyl-(1–4)-deoxyfructosyl, α-glucosyl(1–4)-α-glucosyl(1–4)-deoxyfructosyl.

b) a residue of formula VIb

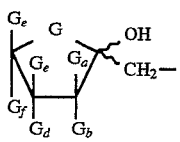

wherein one of radicals $G_a$ and $G_b$ is hydrogen and the other is OH one of radicals $G_c$ and $G_d$ is hydrogen and the other is OH or O-glycosyl, wherein the glycosyl radical is derivable from a reducing mono-, di- or oligosaccharide, one of radicals $G_e$ and $G_f$ is hydrogen and the other is hydrogen, COOH, $CH_2OH$, $CH_2$—O—P(O)—$(OH)_2$ or $CH_2$O-glycosyl, wherein the glycosyl radical is derivable from a reducing mono-, di- or oligosaccharide, e.g. wherein radicals $G_a$ to $G_f$ are selected such that the radical of formula VIb corresponds to a radical which is obtainable by means of an Amadori rearrangement from a natural or a synthetically accessible mono-, di- or oligosaccharide.

Residues of formula VIb may be obtained for example by means of an Amadori rearrangement from saccharides such as gentiobiose, melibiose, ribose, xylose or from uronic acids such as glucuronic acid or galacturonic acid.

In formula II,

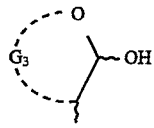

preferably is a) a residue of formula VIIa

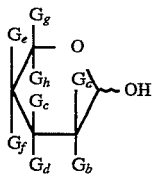

wherein one of radicals $G_a$ or $G_b$ is hydrogen and the other is a free bond, one of radicals $G_c$ or $G_d$ is hydrogen and the other is OH, one of radicals $G_e$ or $G_f$ is hydrogen and the other is OH or O-glycosyl, wherein the glycosyl radical is derivable from a reducing mono-, di- or oligosaccharide, one of radicals $G_g$ and $G_h$ is hydrogen and the other is $CH_2OH$, or $CH_2$—O-glycosyl, wherein the glycosyl radical is derivable from a reducing mono-, di- or oligosaccharide, e.g.

wherein radicals $G_a$ to $G_h$ are selected such that the radical of formula VIIa corresponds to a radical which is obtainable by means of a Heyns rearrangement from a natural or a synthetically accessible mono-, di- or oligoketose.

b) a residue of formula VIIb

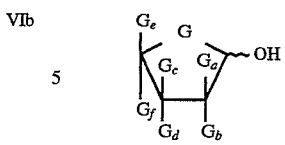

wherein one of radicals $G_a$ and $G_b$ is hydrogen and the other is a free bond, one of radicals $G_c$ and $G_d$ is hydrogen and the other is OH, one of radicals $G_e$ and $G_f$ is hydrogen and the other is $CH_2OH$ or $CH_2$—O-glycosyl, wherein the glycosyl radical is free bond, derivable from a reducing mono-, di- or oligosaccharide e.g. wherein radicals $G_a$ to $G_f$ are selected such that the radical VIIb corresponds to a radical which is obtainable by means of a Heyns rearrangement from a natural or a synthetically accessible mono-, di- or oligoketose.

Residues of formula VIIa or VIIb may be obtained for example by means of Heyns rearrangement from sugar such as D-fructose, lactulose, L-sorbose, D-tagatose or D-ribulose.

In formula III, the polyhydroxymono- or -dicarboxylic acid, e.g contains at least 3 hydroxy groups and may also contain further substituents, e.g. amino or acetylamino groups.

Examples of such polyhydroxycarboxylic acids are:

the "onic acids" derived from sugar, such as gluconic acid, or "aric acids" such as glucaric acid, furthermore, quinic acid, acetylmuranic acid, acetylneuraminic acid or D-glucosaminic acid.

Examples of uronic acids are glucuronic and galacturonic acids.

In the compounds of formula IV, $G_4$, $G_4'$, $G_4''$ and $G_4'''$ have the definitions given above for $G_1$, or $G_2$.

The radical Q or Q' joins a $NH_2$ group of the peptide with a $NH_2$ or HO group of the sugar residue, and is e.g. the radical of a dicarboxylic acid or preferably a —$C_bH_2$—CO— radical wherein b is 0 to 6. The radical may be branched. Q' denotes for example a

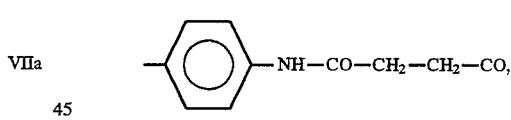

or in particular a —$C_bH_{2b}$—CO— radical (b e.g. 1 to 6). Q is e.g. a —$CH_2$—CO-moiety. Especially Q is —CO— or —CS—. —NH—Q"— and —NH—Q'" denote radicals which join a $NH_2$ group of the peptide with the sugar residue, especially radicals of w-aminocarboxylic acids. They may signify for example a —NH—$C_bH_{2b}$—CO— radical.

In the case of a compound of formula V, preferred are those of formula Va, especially wherein n is 3.

All the above-mentioned residues P are residues of biologically active peptides. Such peptides include all natural and synthetic peptides (also derivatives and analogues thereof (see the beginning of this description) having hormonal, enzymatic or immunomodulatory activity. This activity may be both stimulating and inhibiting. The following may be mentioned as examples of such peptides: somatostatin, calcitonin, oxytocin, vasopressin, insulin, LH, LHRH, GRF, gastrin, substance P, cathepsin, encephalins, as well as all derivatives and analogues of these peptides which have similar activity to the peptides or having antagonising activity.

The compounds of the invention preferably contain at least 8 amino acid units, e.g. 8 to 32, especially 8 to 20, in particular 8 to 10 amino acids.

Preferred peptides are those of formula I and II.

In the above and following formulae, for the sake of simplicity, the sugar radical is usually only represented by the structure of pyranose. Naturally, the furanose and open chain structures are also included in the invention, provided that they exist for the relevant sugars.

The present invention includes processes for the production of compounds of the above formulae. They may be produced by methods which are generally known for the synthesis of compounds of this kind.

The compounds of the invention may be produced for example as follows:

a) at least one protecting group, which is present in a sugar derivatized peptide, is removed, or b) two peptide units, each of which contains at least one amino acid or an amino alcohol in protected or unprotected form and one peptide unit contains the sugar radical, are linked together by an amide bond, wherein the peptide bond is in such a way that the desired amino acid sequence is obtained, and stage a) of the process is then optionally effected, or c) at least one optionally protected residue is introduced into a protected or unprotected peptide and stage a) of the process is then optionally effected, or d) a functional group of an unprotected or a protected sugar derivatized peptide is converted into another functional group or removed, so that an unprotected or a protected glycosylated peptide is obtained, and in the latter case stage a) of the process is effected, or e) a sugar derivatized peptide, in which the mercapto groups of Cys radicals exist in free form, is oxidised to produce a peptide in which two Cys radicals are joined by a S—S— bridge.

As mentioned in the beginning of this description the term "sugar" as used herein also covers sugar derivatives such as amino sugars, oxidized and reduced sugars or esterified sugars.

The above reactions may be effected in conventional manner analogously to the processes described in the following examples, in particular process a) and b) may be effected according to the synthesis of the invention described hereinafter. Where desired, in these reactions, protecting groups which are suitable for use in peptides or sugars may be used for functional groups which do not participate in the reaction. The term protecting group includes a polymer resin having functional groups.

The compounds of formula I may be produced by reacting a protected peptide having a free amino group in a slightly acidic medium with a reducing mono-, di- or oligosaccharide or a corresponding uronic acid or ester thereof (Amadori rearrangement), and subsequently removing the protecting groups.

This reaction may take place in a conventional manner for the Amadori rearrangement. The acid added may be e.g. glacial acetic acid. When reacting with uronic acid, an additional acid can be dispensed with. It is preferable to use an excess of carbohydrate, e.g. ten equivalents for one equivalent of peptide compound. The reaction may be carried out in a polar solvent such as methanol, preferably at temperatures of ca. 60° to 70° C.

The compounds of formula II may be produced by reacting a protected peptide having a free amino group in a slightly acidic medium with a ketose (Heyns rearrangement). The reaction can be carried out under the same conditions as for the Amadori rearrangement (see above).

The compounds of formula III can be produced by reacting a protected peptide having a free amino group with an acid of formula $G_3$—COOH or a reactive derivative of such an acid, and then removing the protecting group(s). This may be a conventional amidation reaction, which can be effected in known manner. The acid halides can be used in particular as the reactive derivatives of carboxylic acids. The amides can e.g. also be produced with the free acids in the presence of hydroxybenzotriazole and dicyclohexylcarbodiimide.

The compounds of formula IVa, IVb, IVc and IVd may be produced by a) reacting the peptide first of all with the bridge member and then reacting the product with the sugar, or b) reacting the sugar first of all with the bridge member and then reacting the glycolysed bridge member with the peptide.

These reactions may be effected in conventional manner. Generally the amide, ester or acetal compounds of the invention are major products. The compounds of the invention may be purified in conventional manner.

Compounds of formula IVa wherein Q is —CO— or —CS— may be produced for example by coupling the corresponding glycosylisocyanate or glycosylisothiocyanate of formula

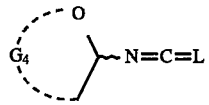

wherein L is O or S and $G_4$ is as defined above and wherein the free hydroxyl groups present in $G_4$ are protected, e.g. by acylation, to a peptide P—$NH_2$ in protected form, and thereafter splitting off the protecting groups.

This reaction may be effected in conventional manner for the production of urea derivatives.

Compounds of formula IVc and IVd may be obtained by means e.g. of an Amadori or Heyns rearrangement, e.g. as described above for the production of compounds of formula I and II.

A compound of formula Va or Vb may be produced e.g. by a') reductive amination of an aldose, deoxyaldose or ketose with the peptide P—$NH_2$, or b') reducing the hemi-acetal group in a compound of formula I or II, wherein if desired-any reactant may be temporarily protected.

The reductive amination and reduction may be effected in conventional manner. The reductive amination may be effected for example with $NaBH_3CN$. The preferred pH is 7. The reduction of the hemi-acetal group may be effected with borohydrides, for example with $NaBH_4$. The preferred pH is about 6.

Insofar as the production of the starting materials is not particularly described herein, it is known or may be produced in conventional manner, e.g. using methods known in the literature or described herein for analogous compounds, or by the synthesis of the invention described hereinafter.

One preferred class of compounds of the invention comprises the sugar derivatives of somatostatin peptides, e.g. of 4 to 9 amino acids. The term somatostatin peptides includes its analogues or derivatives thereof. Especially preferred are the sugar derivatives of compound of formula VIII:

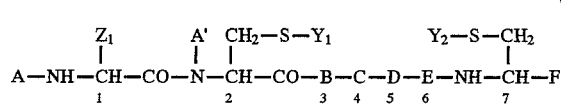  VIII wherein

A is hydrogen, alkyl with 1 to 3 C-atoms or alkanoyl with 1 to 4 C-atoms,

>N—CH($Z_1$)—CO is
1) a (L)- or (D)-phenylalanine residue which is optionally substituted by halogen, $NO_2$, $NH_2$, OH alkyl with 1 to 3 C-atoms and/or alkoxy with 1 to 3 C-atoms, or
2) the residue of a natural lipophilic α-amino acid or of a corresponding (D)-amino acid, other than that given under 1), wherein $Z_1$ in >N—CH($Z_1$)—CO— represents the residue of an amino acid residue defined under 1) and 2), A' is hydrogen or alkyl with 1 to 3 C-atoms, $Y_1$ and $Y_2$, independently of one another, are
1) hydrogen
2)

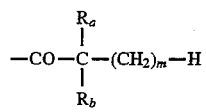

wherein m is a whole number from 1 to 4,
$R_a$ is $CH_3$ or $C_2H_5$ and
$R_b$ is H, $CH_3$ or $C_2H_5$, or

3)

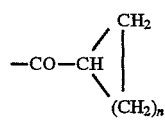

wherein n is a whole number from 1 to 5, or

4) —CO—$NHR_c$ wherein $R_c$ is a straight-chain or branched alkyl radical with 1 to 6 C-atoms, or

5)

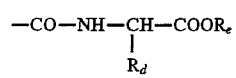

wherein $R_d$ is the residue of a natural α-amino acid (incl. hydrogen) which is located on the α-C-atom, and $R_e$ is an alkyl radical with 1 to 5 C-atoms,

6)

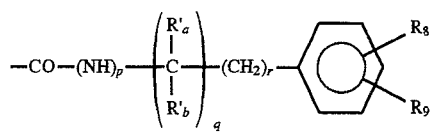

wherein $R_a'$ and $R_b'$, independently of one another, are hydrogen, $CH_3$ or $C_2H_5$, $R_8$ and $R_9$, independently of one another, are hydrogen, F, Cl, Br, alkyl with 1 to 3 C-atoms or alkoxy with 1 to 3 C-atoms, p is 0 or 1, q is 0 or 1, and r is 0, 1 or 2, or $Y_1$ and $Y_2$ together denote a bond, B is Phe or Phe which is substituted in the phenyl radical by F, Cl, Br, $NO_2$, $NH_2$, OH, alkyl with 1 to 3 C-atoms or alkoxy with 1 to 3 C-atoms, C is L- or D-Trp which is optionally substituted in the benzene ring by F, Cl, Br, $NO_2$, $NH_2$, OH, alkyl with 1 to 3 C-atoms or alkoxy with 1 to 3 C-atoms, D is Lys, wherein the α-amino group may be substituted by methyl, E is Thr, Ser, Val, F is $COOR_1$, $CH_2OR_2$, CO—$NR_3R_4$ or

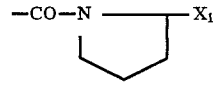

$R_1$ is hydrogen or alkyl with 1 to 3 C-atoms, $R_2$ is hydrogen or the radical of a physiologically acceptable, physiologically hydrolysable ester, $R_3$ is hydrogen, alkyl with 1 to 3 C-atoms, phenyl or phenylalkyl with 7 to 10 C-atoms, but when $R_4$ denotes —CH($R_5$)—$X_1$, it only denotes hydrogen or methyl, $R_4$ is hydrogen, alkyl with 1 to 3 C-atoms or

  IX $R_5$ is the residue of a natural amino acid (including hydrogen) which is located on the α-C-atom, or a HO—$CH_2$—$CH_2$— or HO(—$CH_2$)$_3$ radical, wherein the group IX may have the L- or D-configuration, $X_1$ is $COOR_1$, $CH_2OR_2$ or

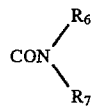

$R_6$ is hydrogen or alkyl with 1 to 3 C-atoms, $R_7$ is hydrogen, alkyl with 1 to 3 C-atoms, phenyl or phenyl alkyl with 7 to 10 C-atoms, wherein the radicals B, D and E exist in the L-form and the radicals in positions 2 and 7, as well as the radicals $Y_1$4) and $Y_2$4) exist independently in the D- or L-form, as well as salts and complexes of these compounds.

Such compounds are disclosed in U.S. Pat. No. 4,395,403 the contents of which including the examples thereof are incorporated herein by reference.

In the polypeptide derivatives of the above formula VIII, the following definitions or combinations thereof are preferred:

If >N—CH($Z_1$)—CO— has definition 1), this residue preferably is a (L)- or (D)-phenylalanine or a (L)- or (D)-tyrosine residue (wherein $Z_1$ signifies benzyl or p—OH), especially the (D)-phenylalanine residue.

If >N—CH($Z_1$)—CO— has definition 2), the residues in which $Z_1$ is alkyl with 3, preferably 4, or more C-atoms, e.g. up to 7 C-atoms are preferred.

The >N—CH($Z_1$)—CO— radical most preferably is a residue defined under 1).

$Y_1$ and $Y_2$ preferably have the significances given above under 1, 2 or 4. Especially they form a bond together.

B preferably denotes Phe or Tyr

C preferably denotes -(D)-Trp

D preferably denotes Lys

E preferably denotes Thr

F preferably denotes

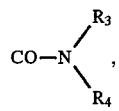

especially

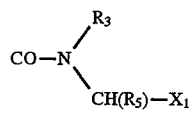

wherein the residue —CH($R_5$)—$X_1$ preferably has the L-configuration $R_3$ preferably denotes hydrogen, $R_5$ denotes $CH_2OH$,

i-butyl, $CH_2CH_2OH$ or $(CH_2)_3$—OH, especially $CH_2OH$ or

in particular

$X_1$ preferably denotes

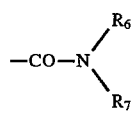

or $CH_2OR_2$, especially $CH_2OR_2$, $R_2$ preferably denotes hydrogen.

$R_2$ as the residue of an ester preferably denotes HCO, alkyl-carbonyl with 2 to 12 C-atoms, phenylalkylcarbonyl with to 12 C-atoms or benzoyl.

The residues in positions 2 and 7 preferably have the L-configuration.

Especially preferred sugar somatostatin derivatives are those which have a sugar residue on the N-terminal amino group, e.g. compounds of formula

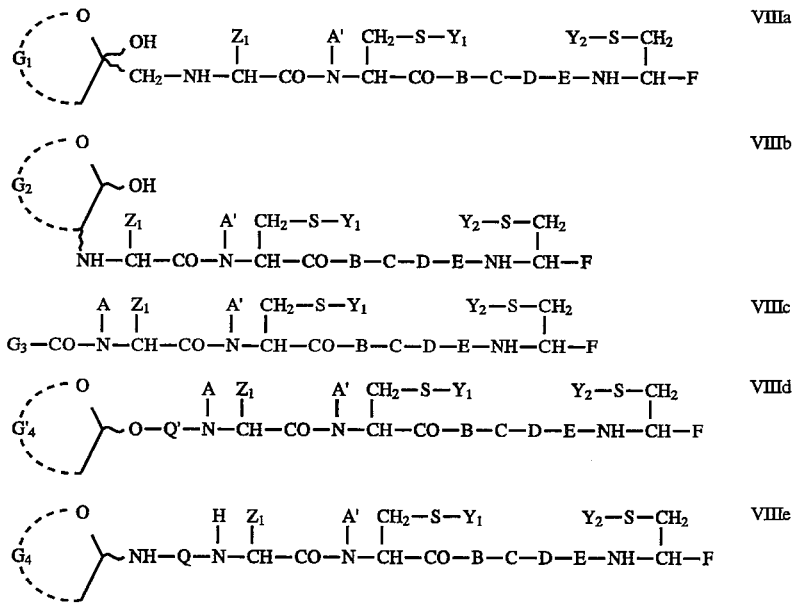

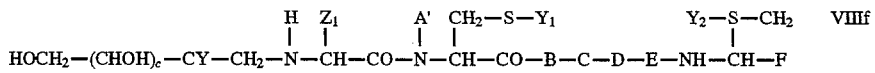

Especially preferred are compounds of formula VIIIa, VIIIb, VIIIe and VIIIf.

A group of compounds comprises those of formula VIIIpa

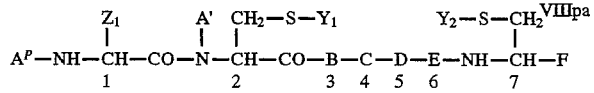

wherein $A^P$ is the deoxy radical of a ketose or a corresponding uronic acid, the group being linked by a $CH_2$ group to the NH group, said desoxy group being obtainable by an Amadori reaction of an aldose or a corresponding uronic acid with the free amino group of the somatostatin, and $Z_1, A', Y_1, B, C, D, E, Y_2$ are as defined above with respect to formula VIII.

Another group of compounds comprises compounds of formula VIIIPb

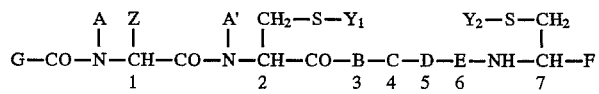

wherein

G is an acyl radical of an uronic acid, a polyhydroxycyclohexanecarboxylic acid, N-acetyl muraminic acid or N-acetyl-neuraminic acid, A is hydrogen, alkyl with 1 to 3 C-atoms, or alkanoyl with 1 to 4 C-atoms, $Z, A', Y_1, B, C, D, E, Y_2$ and F are as defined above.

Conveniently G is glucuronic acid, galacturonic acid or quinic acid.

Another group of compounds comprises those of formula VIIIpc

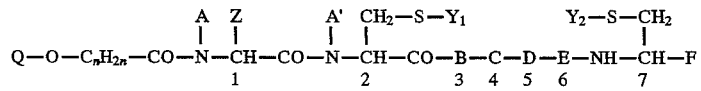

wherein

Q is hydrogen or the glycosyl group of a mono-, di- or oligosaccharide, n is a whole number from 1 to 6, A is hydrogen, alkyl with 1 to 3 C-atoms or alkanoyl with 1 to 4 C-atoms, $Z, A', Y_1, B, C, D, E, Y_2$ and F are as defined above.

A further preferred class of compounds of the invention comprises the sugar derivatives of calcitonins.

The term calcitonin embraces calcitonins which are naturally occurring (whether extracted from natural sources, cell cultures etc or produced synthetically) and derivatives and analogues.

The natural calcitonins which may be used include, human, salmon, eel, chicken, beef, sheep, rat or porcine calcitonin, especially human, salmon, chicken and eel calcitonins.

Derivatives and analogues of these calcitonins include in particular natural calcitonin structures, wherein one or more amino acid radicals are replaced by one or more other amino acid radicals and/or the S—S— bridge is replaced by an alkylene bridge, and/or wherein one or several amino acid radicals have been omitted.

Especially preferred are the sugar derivatives of calcitonins of the following formula X

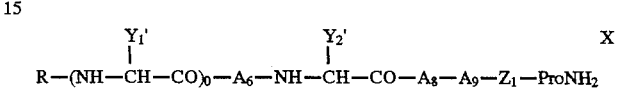

wherein

R is H or R"CO

R"CO is the acyl radical of a carboxylic acid $Y_1'$ is the radical located on the α-C-atom of a α-amino acid, $Y_2'$ the radical located on the α-C-atom of a α-amino acid,

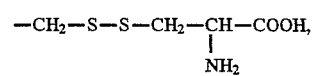

$-CH_2-S-S-CH_2-CH_2-COOH$, $-(CH_2)_s-COOH$ or $-CH_2-S-Y_3$, $Y_3$ is alkyl with 1 to 4 C-atoms; benzyl which is optionally substituted by methyl or methoxy; or $CH_3CONH-CH_2-$, o is a whole number from 1 to 4

$A_6$ is Thr or D-Thr s is a whole number from 3 to 5

$A_8$ is the aminoacyl radical of a neutral, lipophilic L-α-amino acid $A_9$ is the aminoacyl radical of a neutral, lipophilic L- or D-α-amino acid, and $Z_1$ is a polypeptide radical which is located in positions 10 to 31 of a natural calcitonin or a derivative or analogue thereof, which has hypocalcemic activity, wherein the 1 to 4 $Y_1'$ radicals in formula X, independently of one another, may be the same or different and, with the exception of the aminoacyl radical $A_8$, all amino acid radicals in formula X may have the L- or D-configuration, as well as salts and complexes of these compounds.

Such compounds are described for example in GB 2,184,729 A the contents of which as well as the specific examples are incorporated herein by reference.

$Z_1$ in formula X signifies a peptide radical which may be present in positions 10 up to 31 in various known calcitonins, e.g. in human, salmon, eel, chicken, beef, sheep, rat or porcine calcitonin, as well as in derivatives and analogues of these calcitonins, having similar activity. By derivatives and analogues of these calcitonins are understood especially natural calcitonins, wherein one or more amino acid radicals are replaced by one or more other amino acid radicals, or the S—S— bridge is replaced by an alkylene bridge, or wherein one or more amino acid radicals have been omitted. These peptide radicals $Z_1$ normally comprise 22 amino acids, but they may also contain a correspondingly smaller amount of amino acid radicals by omitting one or several amino acid radicals (des-aminoacyl derivatives), $Z_1$ preferably denotes a) Gly-Thr-Tyr-Thr-Gln-Asp-Phe-Asn-Lys-Phe-His-Thr-Phe-Pro-Gln-Thr-Ala-Ile-Gly-Val-Gly-Ala b) Gly-Lys-Leu-Ser-Gln-Glu-Leu-His-Lys-Leu-Gln-Thr-Tyr-Pro-Arg-Thr-Asp-Val-Gly-Ala-Gly-Thr c) Gly-Lys-Leu-Ser-Gln-Glu-Leu-His-Lys-Leu-Gln-Thr-Tyr-Pro-Arg-Thr-Asn-Thr-Gly-Ser-Gly-Thr Compounds of formula X wherein $Z_1$ has the definition given under b) or c), preferably those wherein $Z_1$ has definition c) are especially preferred.

R"CO is preferably the acyl residue of an aliphatic, cycloaliphatic, aromatic or heterocyclic carboxylic acid.

R" is preferably a') saturated or unsaturated, straight-chain or branched alkyl with 1 to 17 C-atoms, especially saturated alkyl with 3 to 9 C-atoms, b') cycloalkyl with 5 to 7 C-atoms or cycloalkylalkyl wherein the cycloalkyl group contains 5 to 7 C-atoms and the alkyl radical contains 1 or 2 C-atoms, c') adamantyl, adamantylmethyl or adamantylethyl, or d') phenyl, benzyl or phenethyl.

In the above-mentioned definitions for R", the alkyl, cycloalkyl or phenyl radicals may be substituted by the usual substituents, e.g. by halogen, $NO_2$, OH, alkoxy, etc.

The residue R"CO may be e.g. the α-desamino residue of a natural α-amino acid. For R", definitions a'), b') and c') are preferred.

$Y_1'$ and $Y_2'$ as radicals which are found on the α-C-atom of an α-amino acid are in particular the radicals which are bonded to the α-C-atom of a natural α-amino acid, but radicals of other α-amino acids may also be contemplated, e.g. of 3-cyclohexylalanine or of an α-aminoisobutyric acid.

When o in formula X signifies 4, a) the N-terminal aminoacyl radical (corresponding to the second amino acid radical in the sequence of the natural calcitonins) is preferably Ser, Gly or Ala, b) the second aminoacyl radical (corresponding to the third amino acid radical in the sequence of the natural calcitonins) is preferably Asn or Ser, c) the third aminoacyl radical (corresponding to the fourth amino acid radical in the sequence of the natural calcitonins) is preferably Leu, Asn, Ser, Phe, D-Leu or the radical of cyclohexylalanine, d) the fourth aminoacyl radical (corresponding to the fifth amino acid radical in the sequence of the natural calcitonins) is preferably Ser or Ala.

When o in formula X is 3, the N-terminal, the second and the third amino acid radicals have the same preferred definitions as above for the case when o=4 under b).

When o in formula X is 2, the N-terminal and the second amino acid radicals have the same preferred definitions as above for the case when o=4 under c) and d).

When o in formula X is 1, the N-terminal and the second amino acid radical is preferably Ser or Ala.

$A_6$ is preferably Thr

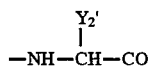

preferably denotes Cys, a derivative of cystein as given above for $Y_2'$, or a neutral lipophilic α-amino-acyl radical, especially, Ala or another neutral lipophilic α-aminoacyl radical, in particular Ala $A_8$ is preferably the aminoacyl radical of a neutral lipophilic α-amino acid, especially Val or Gly $A_9$ is also preferably the aminoacyl radical of a neutral lipophilic α-amino acid, especially Leu or Phe In the compounds of formula X, o is preferably 2, wherein R signifies H or R"CO, or in particular, o is 1 and R is R"CO.

All the amino acid radicals preferably have L-configuration.

The glycosylated calcitonins (including derivatives and analogues) are especially those which are glycosylated on the N-terminal amino group or on one or several amino group(s) in one or several side chain(s), e.g. compounds of formulae

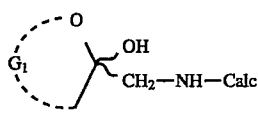 XIa

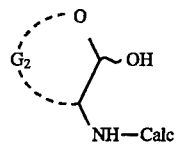 XIb

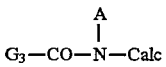 XIc

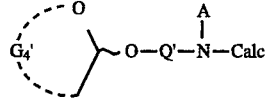 XId

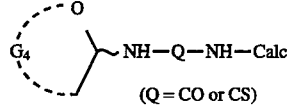 XIe or

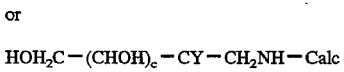 XIf

Calc denotes the residue of a natural calcitonin or of a derivative or analogue of such a calcitonin, which is bonded to the sugar residue via an amino group on the N-terminal end or in a side chain.

The calcitonin derivative of formula X may be produced by methods which are generally known for the synthesis of polypeptides of this kind. The polypeptides of the above formula may be produced for example as follows:

a) at least one protecting group, which is present in a protected polypeptide in the sequence given in formula X, is removed, or b) two peptide units, each of which contains at least one amino acid or derivative thereof, as described for formula X in protected or unprotected form, are linked together by an amide bond, wherein the peptide bond should be made in such a way that the amino acid sequence contained in formula X is obtained, and stage a) of the process is then optionally effected, or c) a compound of formula X, wherein R denotes hydrogen, in protected or unprotected form, is reacted with an acid of formula R"COOH or with a reactive derivative of such an acid, and stage a) of the process is optionally effected, or d) in order to produce a compound of formula X wherein $Y_2'$ denotes

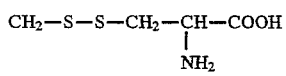

or $CH_2$—S—S—$CH_2$—$CH_2$—COOH, either a compound of formula XII

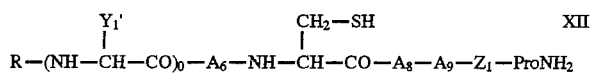

in protected or unprotected form is reacted with a compound of formula XIII

wherein $R_{10}$ is a group which facilitates the formation of a S—S— bridge with the S-atom of the other $CH_2SH$ group in the peptide of formula XII, $R_{11}$ signifies hydrogen or an amino-protecting group $R_{12}$ signifies OH or a protecting group for the carboxyl group, and V signifies hydrogen or a NH group, or a compound of formula XIV

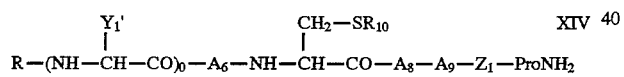

in protected or unprotected form, wherein $R_{10}$ is defined as above, is reacted with a compound of formula XV

and then stage a) of the process is optionally effected.

If the production of the starting products is not specifically described, these compounds are known or may be prepared and purified by the usual methods. The end products of formula X can similarly be purified in the usual way, so that they contain less than 5% polypeptide by-products. The peptides used as starting products for processes a) and b) can similarly be produced in known manner in solution or by the solid phase process.

Production of peptide units which contain a —$CH_2$—S—S—$CH_2$—$CH_2$—COOH or $CH_2$—S—S—$CH_2$—$CH(NH_2)$—COOH group as the $Y_2'$ radical, may take place analogously to the above-mentioned process d).

In this process d), compounds of formula XIII or XIV are used, in which $R_{10}$ denotes the known radicals which react with mercaptans whilst forming a S—S— bond. $R_{10}$ is in particular S-alkyl, —S—COOalkyl,

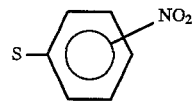

or S—$SO_3$—.

In these radicals, alkyl is especially lower alkyl with 1 to 4 C-atoms. The introduction of these radicals into compounds having free SH groups may be effected analogously to methods which are known in sulphur chemistry.

A further preferred class of compounds comprises a group of LH RH antagonists.

Preferably the compounds include sugar derivatives of compounds of formula XVI

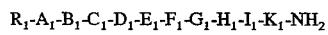 XVI wherein $R_1$ is H or an acyl group of 1 to 7 C-atoms, $A_1$ is D-Phe, which is optionally substituted in the phenyl ring by F, Cl, Br, $NH_2$, $CH_3$, or $OCH_3$, especially in the 4 position, β-D-naphthylalanine, D-Trp which optionally is substituted in the 5 or 6 position by F, Cl, Br, $NH_2$, or $OCH_3$ and/or is substituted in position 1 by formyl or acetyl-, proline, 3,4-dehydroproline or D-pyroglutamine, $B_1$ is D-Phe optionally substituted by F, Cl, Br, $NH_2$, $CH_3$ or $CH_3O$ in the phenyl ring, D-α-methylphenylalanine, which is optionally substituted in the 4 position, by Cl, or β-D-Naphthylalanine.

$C_1$ is D-Trp optionally substituted in position 5 or 6 by F, Cl, Br, $NH_2$ and/or $OCH_3$ and/or in position 1 by HCO or $CH_3CO$, β-D-naphthylalanine, 3-D-pyridylalanine, D-Tyr, or Phe optionally substituted by F, Cl, Br, $NH_2$, $CH_3$, or $CH_3O$, $D_1$ is Ser, $E_1$ is Tyr, or phenylalanine optionally substituted by Cl, Br, $NH_2$, $CH_3$ or $CH_3O$, in the phenyl ring, $F_1$ is D-Phe, optionally substituted in the phenyl ring by F, Cl, Br, $NH_2$, $CH_3$ or $CH_3O$, D-Trp optionally substituted in position 5 or 6 by F, Cl, Br, $NH_2$ or $CH_3O$ and/or in position 1 by formyl or acetyl, D Tyr, β-D-naphthylalanine, D-Leu, D-Ile, D-Nle, DVal, D-Ser (OtBu), D-Arg, optionally dialkylated with ($C_{1-6}$)alkyl or ($C_{5-6}$)cycloalkyl, D-homoarginine, optionally dialkylated with ($C_{1-6}$)alkyl or ($C_{5-6}$)cycloalkyl, D-His, D-His(Bzl), D-Lys, or D-Orn, both optionally dialkylated with ($C_{1-6}$)alkyl or ($C_{5-6}$)cycloalkyl, D-Phe (p——$NH_2$) or α-p-aminocyclohexylalanine, $G_1$ is Leu, Nle, Nva, N-α-methylleucine, Trp, Phe, Met or Tyr, $H_1$ is Arg, Lys or Orn which optionally is substituted by ($C_{1-6}$)alkyl or ($C_{5-6}$)cycloalkyl, $I_1$ is Pro, hydroxyproline, or 3,4-dehydroproline, and $K_1$ is D-Ala.

If desired $E_1$ and $F_1$ may be replaced by the other $D_1$ and $K_1$, if desired may be Cys which are linked by a S—S— bridge.

If desired one of $D_1$ and $K_1$ is Asp or Glu and the other is Orn, diaminoproponic acid or diaminobutyric acid and wherein the residue $D_1$ and $K_1$ are linked by an amide bridge.

Preferred significances are:

$R_1$=acetyl or formyl $A_1$=D-Phe, D-Phe (p-Cl), β-D-naphthylalanine, 3,4-dehydroproline, $B_1$=D-Phe optionally substituted as indicated above $C_1$=D-Trp optionally substituted as indicated above $D_1$=Ser Optional substitution is preferably mono substitution.

(i) $E_1$=Tyr or Phe optionally substituted as indicated above, when $F_1$=D-Phe or Lys or (ii) $E_1$=D-Phe or Lys when $F_1$=Tyr or Phe optionally substituted as defined above, $G_1$=Leu $H_1$=Arg $I_1$=Pro $K_1$=D-Ala In the above mentioned LHRH antagonists the sugar residue is preferably attached to the N-terminal amino group or to a free amino group in a side chain.

The sugar derivatives preferably have the following structures wherein $H_2$N-LHRH antagonist denotes a LHRH antagonist of formula XVI:

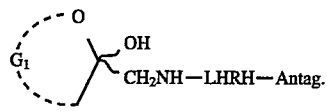 XVIa

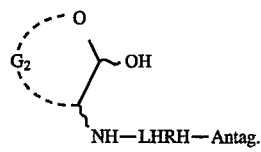 XVIb $G_3$—CO—NH—LHRH—Antag.   XVIc

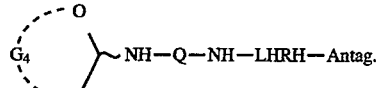 XVId

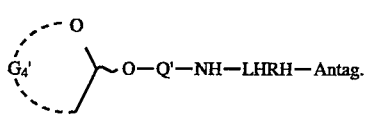 XVIe

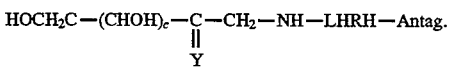 XVIf

In the above defined formulae XVIa to XVIf for simplicity only one sugar moiety is shown bound to a amino group. However, if desired more than one sugar moiety may be present. Preferably two such sugar moieties are present.

The starting materials and the synthesis for the non-modified LHRH antagonists are for example described in EPA 81887 and 201260 A.

Further preferred polypeptides are:
a) oxytocin and vasopressin, as well as their derivatives, e.g. Lys$^8$-vasopressin and Orn$^8$-vasopressin,
b) Insulin
c) Growth hormone releasing factor The starting materials and compounds of the invention may be produced by liquid phase or the solid phase synthesis.

The compounds of the invention may be conveniently prepared by solid phase synthesis.

We have found an especially convenient process for the production of peptide alcohols, which at the C-terminal end of the peptide chain bear two alcohol groups or one alcohol group and one thiol group. The process is especially suitable for the production of peptide alcohols which contain a C-terminal threoninol, serinol or cysteinol radical.

Examples of suitable compounds include some of the somatostatin compounds described herein.

Solid-phase peptide synthesis has proved to be an especially rapid and favourable process for the production of peptides, and has therefore become a generally conventional method.

As is known, first of all an amino acid is bonded by its carboxyl group, forming an ester or amide group, to a hydroxyl group or amino group of an insoluble synthetic resin; then, the further amino acids are added onto this in the desired sequence, and finally the complete polypeptide is cleaved from the carrier resin.

This synthesis operates without problems for normal polypeptides having C-terminal amino acids. However, polypeptide alcohols, which at the C-end bear an amino-alcohol instead of an amino acid, do not easily form a bond with carrier resins bearing OH— or $NH_2$— groups and/or are not so easily cleaved again when synthesis has ended.

The following have previously been proposed as possible solid-phase processes for the production of peptide alcohols:

a) conventional preparation of the corresponding polypeptide containing at the C-end an amino acid (as the ester of a resin bearing OH groups) and subsequent cleavage by reduction, using boron hydrides, the carboxyl group being simultaneously converted into an alcohol function. (U.S. Pat. Nos. 4,254,023/4).

b) Addition of the terminal amino alcohol as ether to a hydroxymethyl resin, using carbonyl diimidazole, and finally, after synthesis of the peptide, cleavage using HCl/TFA or HBr/TFA (Kun-hwa Hsieh and G. R. Marshall, ACS National Meeting, New Orleans, 21–25. 3. 1977).

However, these methods both require drastic cleavage conditions.

We have found that the cleavage of the peptide from the resin, whilst simultaneously forming the C-terminal peptide alcohol, is carried out under mild conditions if the C-terminal amino-alcohol is joined to the resin by an acetal bond.

In accordance with the invention, the peptide alcohol which at the C-terminal end of the peptide chain bears 2 alcohol groups or one alcohol group and one thiol group is produced by acid hydrolysis of an acetal of the peptide alcohol and a polymer resin bearing formylphenyl groups. This is referred to as the synthesis of the invention.

The reaction may be illustrated schematically as follows:

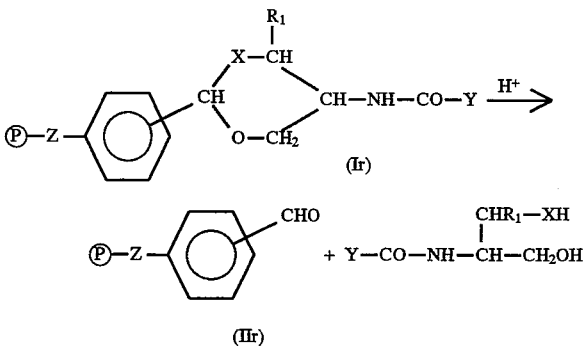

wherein

Ⓟ is the residue of an insoluble synthetic resin

Z is a direct bond or a residue which joins the resin with the (acetalised) formylphenyl group X is O or S $R_1$ is hydrogen or methyl, and Y is the residue of a peptide alcohol which e.g. may bear protecting groups, wherein the optionally acetalised CHO— group is located in the m- or p-position to the radical Z. For simplicity, in formulae I and II of the above scheme, only one substitution group was indicated on the resin; it should however be clear that a number of such groups are bonded to a molecule of the resin polymer. Cleavage of the peptide alcohol from the resin by hydrolysis of the acetal group takes place as mentioned above under acidic conditions, e.g. with diluted trifluoroacetic acid. Hydrolysis can be effected at room temperature.

If Z in formula $I_r$ is a direct bond, the phenyl radicals bearing acetal groups are directly bonded to the polymer residue and belong to the polymer. Examples of such compounds of formula $I_r$ are the acetals of a formylated polystyrene resin (in formula $I_r$, 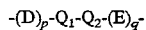 is then a polyethylene chain).

If Z is a residue, then this residue contains a group which is the result of a reaction of a reactive group, that is directly or indirectly bonded to the polymer, with another reactive group, that is directly or indirectly bonded to the (acetalised) formylphenyl group. The radical Z may be represented for example by the following formula IIIr:

$$-(D)_p-Q_1-Q_2-(E)_q- \qquad \text{IIIr}$$

wherein $Q_1$=the residue of a reactive group which is bonded to the polymer $Q_2$=the residue of a reactive group which is bonded to the (acetalised) formylphenyl group D=a residue which joins the group $Q_1$ with the polymer E=a residue which joins the group $Q_2$ with the (acetalised) formylphenyl group p and q, independently of one another, are 0 or 1.

The $Q_1-Q_2$ group is preferably an ester or amide group, especially a carbonamide group. $Q_1$ is preferably NH and $Q_2$ is preferably CO.

D and E, independently of one another, are for example alkylene or alkyleneoxy radicals having 1 to 5 C-atoms. Examples of such compounds of formula Ir, wherein Z is a residue of formula IIIr, are compounds wherein ⓟ-D-$Q_1$ is the residue, of an aminomethylated polystyrene resin and the residue

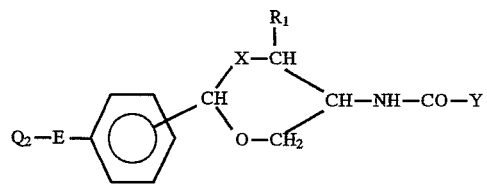

is a residue of formula IVr

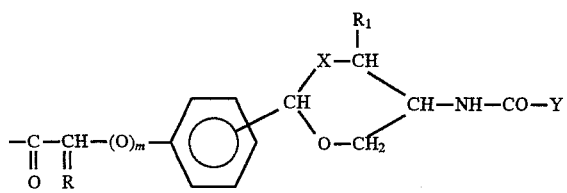

wherein

R=hydrogen or methyl and m=0 or 1, whereby the acetal group is again located in m- or p-position.

In this case, Z is thus

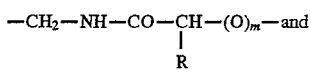

ⓟ is polystyrene.

Radical IVr is preferably

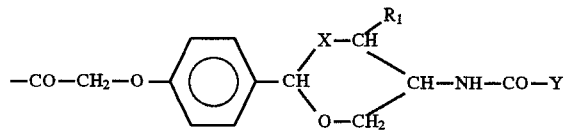

Instead of the aminomethylated polystyrene, other polymers can also be used, especially those having free $NH_2$ groups, e.g. polyacrylamides bearing aminoethyl groups.

As mentioned above, the acetalised formylphenyl group is preferably bonded to the polymer by an amide bond. This ensures that the bonding of the acetalised formylphenyl radical to the resin during synthesis of the polypeptide and during cleavage is stable, and that cleavage occurs on the acetal bond as desired, so that on the one hand the peptide alcohol is generated and on the other hand the formylphenyl radical remains on the resin.

If desired, the peptide alcohol can be attached further away from the resin by incorporating so-called spacers between the reactive groups of the polymer (especially amino groups) and the reactive groups of the acetalised formylphenyl derivative (especially carboxyl groups). For certain reactions on the polypeptide alcohol, this may advantageously be before cleavage (e.g. oxidation of cystein radicals). In this case, the radical D or E in formula IIr additionally contains the spacer and $Q_1$ or $Q_2$ is the reactive radical of the spacer.

The spacer used can be for example a ω-aminocarboxylic acid, such as ε-aminocaproic acid.

In a specific case, when using aminomethylated polystyrene, a radical of formula IVr and ε-aminocaproic acid as the spacer, Z is

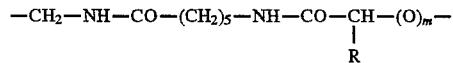

The compounds of formula $I_r$ can be produced by methods which are usual in solid-phase technology, starting with a compound of formula Vr

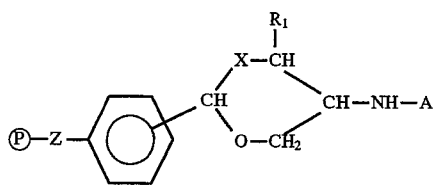         V wherein A is a-protecting group of the amino function and the acetal group is in m- or p-position to the radical Z. For this purpose, first of all the protecting group A is cleaved and then the free amino group is reacted with the next N-protected amino acid etc., until all the amino acids have been added onto the resin in the sequence corresponding to the desired peptide alcohol.

The amino protecting groups to be chosen for the amino acids used or for the amino alcohol must be those which are cleaved under non-acidic conditions, since under acidic conditions hydrolysis of the acetal group takes place. The $CF_3CO—$ or the FMOC— group (9-fluorenylmethyloxycarbonyl) can be used e.g. as such amino protecting groups. These protecting groups are cleaved in a basic medium in a manner which is usual for peptide chemistry.

Only protecting groups in the side chains and the amino protecting group of the last administered amino acid may be acid labile and then are simultaneously split off from the resin with the regeneration of the peptide alcohol.

Preferably the Boc groups present as a protecting group.

As bases are preferably used KOH or piperidine or $NaBH_4$.

The building up of the peptide chain may be effected in conventional manner from a peptide moiety having free amino groups and an amino acid with free or activated carboxyl groups.

The reaction may be effected with the addition of e.g. hydroxybenzotriazol and dicyclohexylcarbodiimide.

Compounds of formula Vr may be produced for example by a) reacting a resin carrying an aldehyde group of formula $II_r$

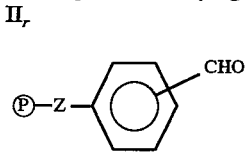         $II_r$ wherein the CHO group is in the m or p position to the Z substituent, with an N-protected amino alcohol of formula

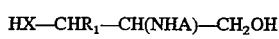

optionally in activated form, or b) reacting a resin having the formula

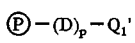

with a compound of formula VIr

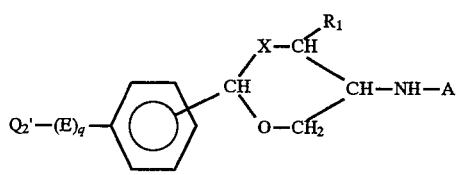         VIr wherein the acetal group is in the m or p position to the $Q_1'$—$(E)_q$— group and $Q_1'$ and $Q_2'$ are two reactive groups which react together to form a $Q_1$–$Q_2$ bridge.

The acetalization of process a) may be effected in the presence of an acid as catalyst. Suitable acids include p-toluene sulphonic acid and p-trifluoromethylsulphonic acid.

If desired a trimethylsilyl group may be used as a protecting group for a free alcohol.

The esterification process b) may be effected under very mild conditions, e.g. by reaction of a carboxylic acid derivative with an OH or $NH_2$ group carrying polymer.

The compounds of formula VIr may be produced by acetylation of a compound of formula

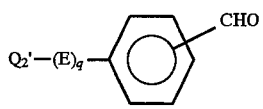

with a compound of formula

HX—$CHR_1$—CH(NHA)—$CH_2OH$

The acetylisation may be effected as for process a).

During the building up and the splitting off of the peptide alcohol from the resin, further reactions may be effected, e.g. removal of protecting groups, e.g. S-protecting groups, or oxidation of cystein radicals.

Such reactions may be effected after splitting off of the peptide alcohol in the liquid phase.

According to the synthesis of the invention pharmacologically active and other peptides which on the C-end contain 2 alcohol groups or an alcohol and a thiol group may be simply produced.

In the following examples, all temperatures are given in degrees celsius and the $[\alpha]_D^{20}$ values are uncorrected. The following abbreviations are used:

AcOH=acetic acid
Boc=tert. butyloxycarbonyl
$Bu^t$=tert. butyl
DCCI=dicyclohexylcarbodiimide
DMF=dimethyl formamide
Fmoc=9-fluorenylmethoxycarbonyl
MeOH=methanol
$NEt_3$=triethylamine
Thr-ol=threoninol radical=$CH_3$—CHOH—CH($CH_2OH$)—NH—
TFA=trifluoroacetic acid
HOBT=N-hydroxybenzotriazole
hpGRF=human pancreatic growth hormone releasing factor
HOSu=N-hydroxy-succinimide All peptides are obtained as polyacetates-polyhydrates with a peptide content of 70 to 90%, HPLC analysis shows that the peptides contain less than 5% of other peptides.

The factor "F" mentioned in the following examples shows the peptide content in the products obtained (F=1 conforms with 100% peptide content). The difference up to 100% [(1-F)×100] consists of acetic acid and water.

All sugars have the α-configuration unless otherwise stated. Deoxy=Desoxy.

EXAMPLE 1

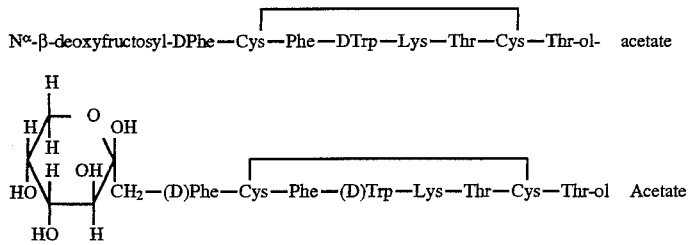

3 ml of trifluoroacetic acid (100%) are added to 400 mg of

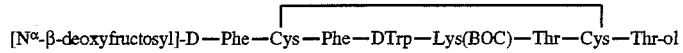

and kept at room temperature until all the starting material has dissolved (5 minutes). After adding 20 ml of diisopropylether, the title compound is precipitated and subsequently filtered off and washed with diisopropylether. The title compound is purified by chromatography on silica gel (eluant: $CHCl_3/MeOH/HOAc/H_2O$ 7/3/0.5/0.5) and is isolated as a white lyophilisate. $[\alpha]_D^{20}$: −31.3° (c=0.52 in HOAc 95%). F: 0.88

The starting product may be produced as follows:

a)

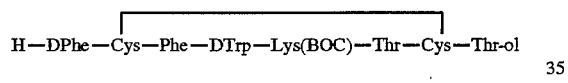

2.25 g of di-tert.butyl-percarbonate, dissolved in 30 ml of DMF, are slowly added in drops at room temperature to a solution of 10 g of

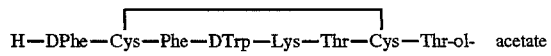

in 100 ml of DMF. After two hours at room temperature, the solvent is drawn off-.under-vacuum, and 200 ml of diisopropylether are added to the residue. The deposit which is being formed is filtered off, washed with diisopropylether and dried. The crude product is purified by chromatography over silica gel (eluant: $CH_2Cl_2/MeOH$ 9/1) and is then isolated as a white amorphous powder. $[\alpha]_D^{20}$: 29.8° (C=1.28 in DMF)

b)

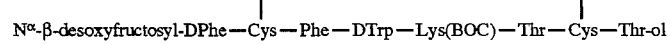

2 g of D-(+)-glucose and 0.5 g of the end product of stage a) are dissolved in 20 ml of MeOH/HOAc 9/1 (v/v), and kept at 60°–70° C. for three hours. After concentration by evaporation, the product is taken up in a little methanol, and the title compound is precipitated with diisopropylether. It is purified by chromatography over silica gel (eluant: $CH_2Cl_2/MeOH$ 9/1). An amorphous powder is obtained. $[\alpha]_D^{20}$= 12.0° (c=1.04 in DMF)

The following compounds (all as acetates) were produced analogously to example 1 (in these compounds, SMS denotes the polypeptide radical

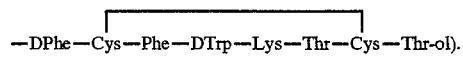

EXAMPLE 2

$N^\alpha$-[α-glucosyl(1–4)-dioxyfructosyl]-SMS

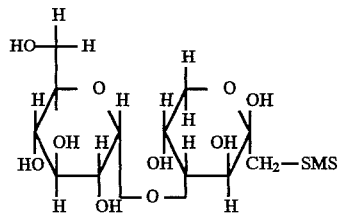

starting with D(+)-maltose instead of D-glucose $[\alpha]_D^{20}$=− 7.9° (c=0.71 in AcOH 95%) F: 0.91

EXAMPLE 3

Nα-[α-glucosyl(1–4)-α-glucosyl(1–4)-β-deoxyfructosyl-SMS

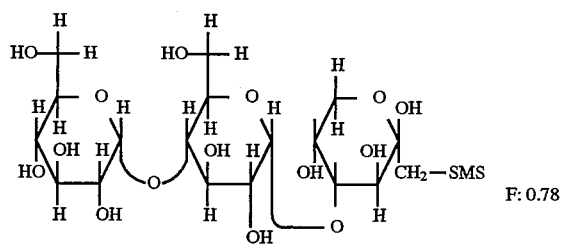

F: 0.78 starting with maltotriose instead of D-glucose $[\alpha]_D^{20}=+11.3°$ (c=0.71 in 95% AcOH)

EXAMPLE 4

Nα-fructofuranuronic Acid-SMS

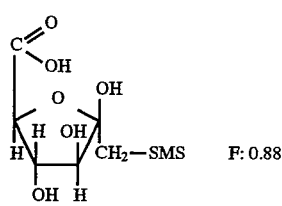

F: 0.88 starting with D-glucuronic acid instead of D-glucose $[\alpha]_D^{20}=-29.4°$ (c=0.34 in 95% AcOH)

EXAMPLE 5

Nα-deoxysorbosyl-SMS

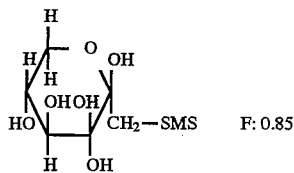

F: 0.85 starting with D (+)-galactose instead of D-glucose $[\alpha]_D^{20}=-30.4°$ (c=0.50 in 95% AcOH)

EXAMPLE 6

Nα-[O-β-D-glucosyl-(1–4)-deoxyfructosyl]-SMS

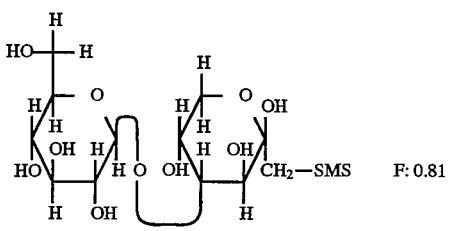

F: 0.81 starting with D(+)-cellobiose $[\alpha]_D^{20}=-28.1°$ (c=0.47 in 95% AcOH)

EXAMPLE 7

Nα-L(–)-deoxyfructosyl-SMS

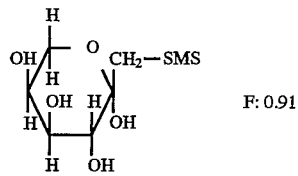

F: 0.91 starting with L(–)-glucose instead of D(+)-glucose $[\alpha]_D^{20}=-20°$ (c=0.46 in 95% AcOH)

EXAMPLE 8

Nα-[O-β-D-glucosyl-(1–6)-deoxyfructosyl]-SMS

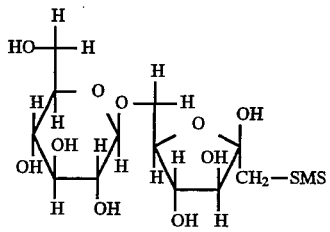

starting with gentiobiose instead of D-glucose $[\alpha]_D^{20}=23.5°$ (c=0.46 in 95% AcOH) F: 0.76

EXAMPLE 9

Nα-[O-β-D-galactosyl-(1–4)-deoxyfructosyl]-SMS

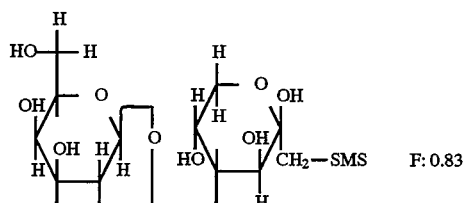

F: 0.83 starting with D(+)-lactose instead of D-glucose $[\alpha]_D^{20}=-29.3°$ (c=0.55 in 95% AcOH)

EXAMPLE 10

N^α-(O-α-galactosyl-(1–6)-deoxyfructosyl)-SMS

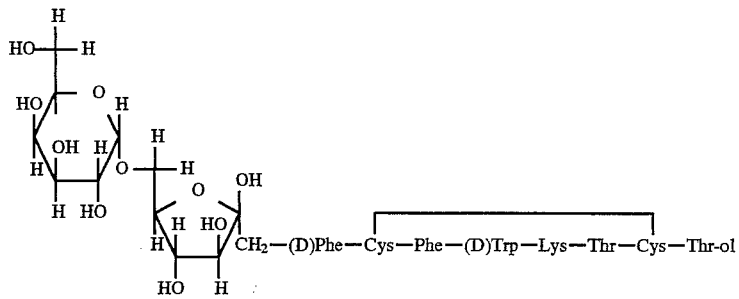

starting with melibiose instead of D-glucose $[\alpha]_D^{20}=+8.4°$ (c=0.5 in 95% AcOH) F: 0.76

EXAMPLE 11

[N-(1-deoxy-D-fructosyl)-Tyr³]-SMS

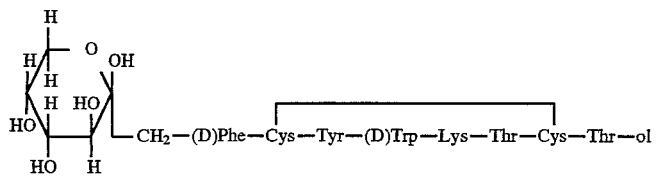

starting with Tyr³-SMS instead of SMS $[\alpha]_D^{20}=-32.2°$ (c=0.9 in 95% AcOH) F: 0.87

EXAMPLE 12

[N-(α-D-Glucopyranosyl-(1–4)-1-deoxyfructosyl), Tyr³]-SMS

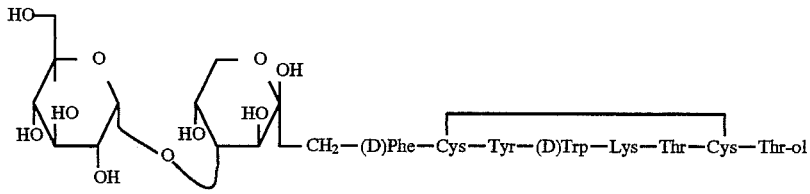

starting with D(+)-maltose instead of D-glucose and Tyr³-SMS instead of SMS $[\alpha]_D^{20}=-4.7°$ (c=1.0 in 95% AcOH) F=0.81

EXAMPLE 13

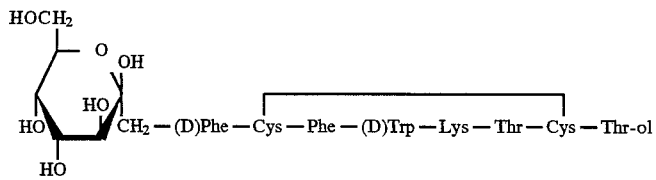

starting with D-glucoheptose instead of D-glucose $[\alpha]_D^{20}$= −12.9° (c=1.0 in 95% AcOH)

EXAMPLE 14

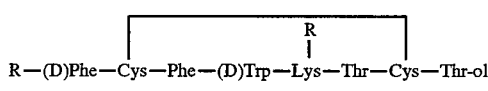

R = 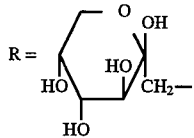

starting with D(+)-glucose and SMS, which does not have a protecting group on the ε-NH₂ group of lysine $[\alpha]_D^{20}$= −42.4° (c=0.37 in 95% AcOH) F=0.83

EXAMPLE 15

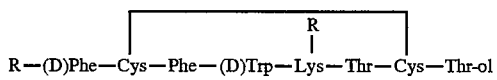

-continued

R = 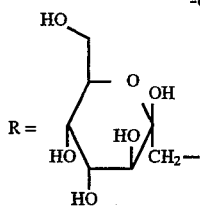

starting with glucoheptose and SMS which does not have a protecting group on the ε-NH₂— group of the lysine $[\alpha]_D^{20}$= −9.3+ (c=0.41 in 95% AcOH) F=0.84

EXAMPLE 16

Fructosyl-6-phosphat-SMS

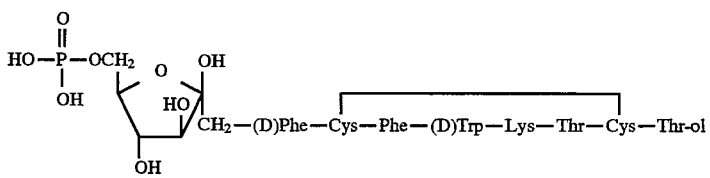

starting from D-glucose-6-phosphate instead of D-glucose $[\alpha]_D^{20}$=−19.5° (c=1.0 in 95% AcOH) F=0.89

EXAMPLE 17

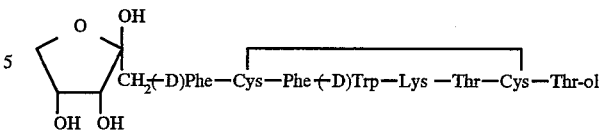

starting from D-ribose instead of D-glucose $[\alpha]_D^{20}$=−31.8° (c=1.0 in 95% AcOH)

EXAMPLE 18

$N^\alpha$-deoxyfructosyl-(D)Phe-Cys[COC(CH₃)₃]-Phe-(D)-Trp-Lys-Thr-Cys [COC(CH₃)₃]-Thr-ol a)

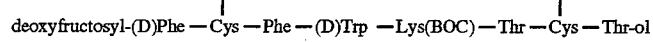

0.58 g of the compound of example 1 in 10 ml of DMF are mixed with 0.08 ml of NEt₃, then with 0.12 ml of (BOC)₂O. The mixture is stirred for ca. 15 hours at room temperature, concentrated under vacuum and agitated with ether. The precipitated product is filtered off. The residue is dissolved with a little MeOH, then the product is precipitated by adding H₂O. The product is filtered, washed with a little H₂O, dried and the title compound is obtained. $[\alpha]_D^{20}$= +14.5° (c=0.7 in DMF)

b) $N^\alpha$-deoxyfructosyl-(D)-Phe'-Cys-Phe-(D)Trp-Lys (BOC)-Thr-Cys-Thr-ol 0.51 g of the end compound of stage a) in a mixture of 10 ml of dioxane and 2 ml of NEt₃/AcOH buffer pH 8.6 under argon is mixed with a total of 0.4 g of dithioerythritol. The mixture is stirred for ca. 15 hours at room temperature and concentrated under vacuum. The precipitated product is centrifuged off. The residue is washed with a little H₂O, then vacuum-dried. The title compound is obtained. $[\alpha]_D^{20}$=+ 3.8° (c=0.8 in DMF)

c) $N^\alpha$-deoxyfructosyl-(D)Phe'-Cys[COC(CH₃)₃]-Phe-(D) Trp-Lys-(B)C)-Thr-Cys(COC(CH₃)₃]-Thr-ol 0.38 g of the end compound of stage b) are dissolved under argon in 25 ml of N-methylpyrrolidone, then mixed at 0° with 0.3 ml of N-methylmorpholine and 0.31 ml of pivaloylchloride, and stirred for ca. 16 hours at 0°. The product is agitated with ether/diisopropylether. The precipitated product is centrifuged off. The residue is dissolved with a little DMF and the product precipitated by adding MeOH and $H_2O$. The product is centrifuged. The residue is vacuum-dried and used further without further purification.

d) $N^\alpha$-deoxyfructosyl-(D)Phe-Cys[COC(CH$_3$)$_3$]-Phe-(D)Trp-Lys-Thr-Cys[COC(CH$_3$)$_3$]-Thr-ol The residue of stage c) is dissolved at 0° in 5 ml of TFA/$H_2O$ (9:1) and stirred for 15 minutes. The product is precipitated by adding a mixture of ether/10% 5n HCl/ether. The product is filtered, washed with ether and dried. The residue is purified by chromatography on silica gel in a mixture of CHCl$_3$/MeOH/AcOH/$H_2O$. Fractions which contain the desired product are combined, concentrated under vacuum whilst adding $H_2O$, then lyophilised. The title compound is obtained. $[\alpha]_D^{20}=-15.3°$ (c=1.0 in 95% AcOH) F: 0.88 used in the protecting group cleavage (BOC cleavage) without being purified.

1 g of the crude product obtained is mixed with 20 ml of tri-fluoroacetic acid (100%) and kept at room temperature until the entire starting material has dissolved (5 minutes). By adding 200 ml of diisopropylether, the title compound is precipitated and subsequently filtered off and washed with diisopropylether. The title compound is purified by chromatography on silica gel (eluant: CHCl$_3$/MeOH/HOAc/$H_2O$ 7/3/0.5/0.5) and is isolated as a white lyophilisate. $[\alpha]_D^{20}=-6.7°$ (c=0.3 in HOAc 95%) F: 0.73

As second product the following 1:1 mixture of isomers having the inverse configuration at $C_2$ of the carbohydrate moiety may be obtained:

EXAMPLE 19

2-[(D)Phe—Cys—Phe—(D)Trp—Lys—Thr—Cys—Thr-ol]-2-deoxy-D-glucose

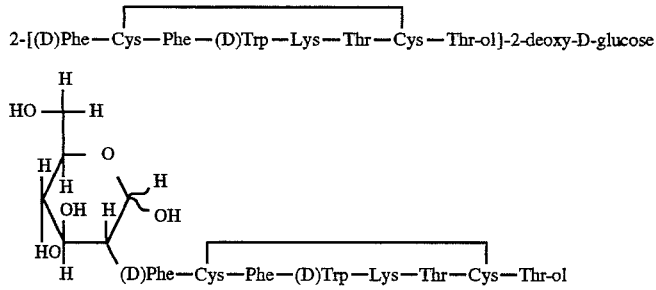

2 g of D(–)-fructose and 1 g of

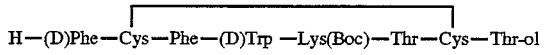

(produced as described in example 1a) are dissolved in 100 ml of MeOH/HOAc 9/1 and kept at 65° C. for 16 hours. After concentration by evaporation, the product is dissolved

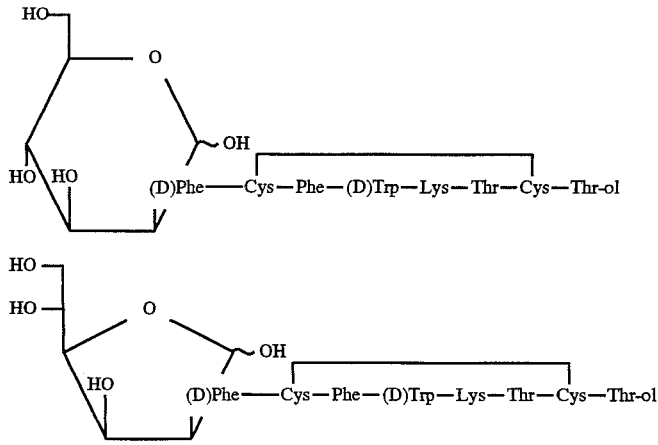

in a little methanol, and the crude product is precipitated with diisopropylether. The crude product thus obtained is

EXAMPLE 20

2-[Tyr³-SMS]-2-dioxy-D-glucose

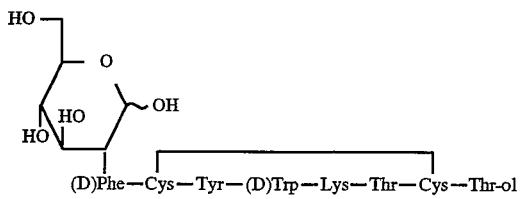

In analogy to example 19 starting from Tyr³ SMS instead of SMS the heading compound is produced. $[\alpha]_D^{20}=-2.9°$ (c=1.0 in 95% AcOH) F=0.95

EXAMPLE 21

Glucoronic Acid Amide of

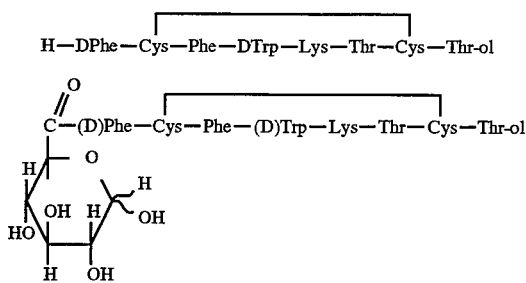

170 mg of the glucuronic acid amide of

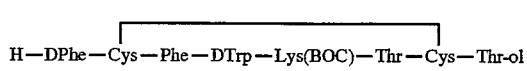

are treated with 3 ml of trifluoroacetic acid 100%) until a complete solution is obtained (5 minutes). The title compound is subsequently precipitated as the trifluoroacetate by adding 20 ml of diisopropylether, and after filtration, drying and subsequent chromatography on silica gel (eluant: CHCl₃/MeOH/HOAc/H₂O 7/3/0.5/0.5), the title compound is isolated in pure form as a white lyophilisate (acetate). $[\alpha]_D^{20}=-29.2°$ (c=0.48 in HOAc 95%)

The starting product may be produced as follows:

A solution of 135 mg of DCCI in 2 ml of DMF is added to a solution, cooled to -30° C., in DMF of 450 mg of

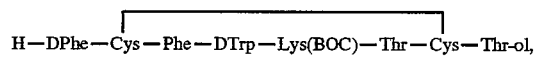

117 mg of glucuronic acid and 135 mg of HOBT. After 48 hours, with simultaneous thawing to room temperature, the resultant dicyclohexylurea is filtered off and the title compound is precipitated by adding 20 ml of diisopropylether. After filtration, drying and chromatography over silica gel (eluant: CH₂Cl₂/MeOH 9/1), the title compound is isolated in pure form $[\alpha]_D^{20}=+16.7°$ (c=0.50 in DMF)

EXAMPLE 22

Quinic Acid Amide of

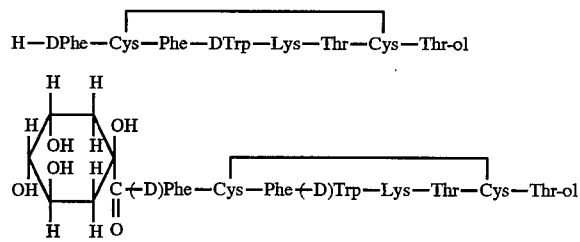

The title compound Was obtained analogously to example 21, starting with L(-)-quinic acid. $[\alpha]_D^{20}=-50°$ (c=0.44 in 95% AcOH) F: 0.97

EXAMPLE 23

Sialic Acid Amide of

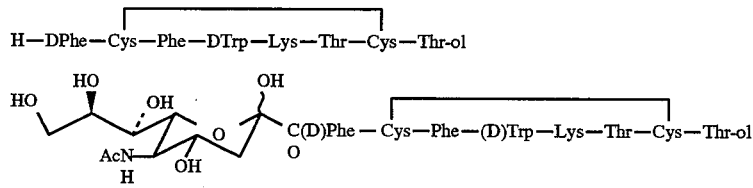

The title compound was obtained analogously to example 21, starting with sialic acid. $[\alpha]_D^{20}=-60.8°$ (c=0.6 in 95% AcOH) F: 0.95

EXAMPLE 24

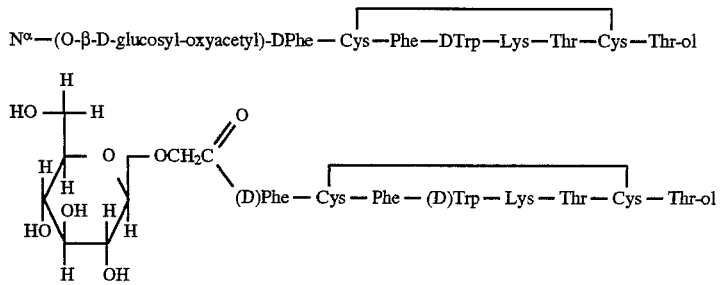

250 mg of

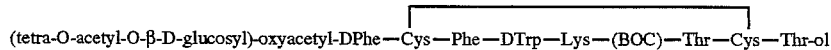

are dissolved in 10 ml of methanol and adjusted to a pH of 10 with a few drops of 1N NaOCH₃ solution in methanol. After reacting for 15 minutes, the solution is neutralised with an ion exchanger (e.g. AMBERLYST® 15, H⁺), and the ion exchanger is filtered off. The filtrate is concentrated and the residue treated for 5 minutes with 3 ml of trifluoroacetic acid. The title compound is precipitated as the trifluoroacetate by adding 20 ml of diisopropylether, and is isolated in pure form as a white lyophilisate after filtration, drying and chromatography on silica gel (eluant: CHCl₃/MeOH/HOAc/ H₂O 7/3/0.5/0.5). $[\alpha]_D^{20}=-39.2°$ (c=0.60 in HOAc 95%) F: 0.91

The starting product may be produced as follows:

a) tetra-O-acetyl-O-β-D-glucosyl-glycolic acid benzylester 2.5 g of molecular sieve 4 Å, powder are added to a solution of 830 mg of glycolic acid benzylester in 50 ml of CH₂Cl₂, and after adding 2.8 g of silver trifluoromethane sulphonate, a solution of 4.1 g of acetobromoglucose in 50 ml of CH₂Cl₂ is added in drops. After 15 minutes, the reaction is stopped with 4 ml of pyridine, the solid constituents are filtered off, and the filtrate is shaken out with 10% NaHSO₄ solution. The title compound is isolated in pure form after chromatography over silica gel (eluant: CH₂Cl₂/ MeOH 99/1). $[\alpha]_D^{20}=-22.4°$ (c=1.7 in CHCl₃)

b) tetra-O-acetyl-O-β-D-glucosyl-glycolic acid 800 mg of tetra-O-acetyl-O-β-D-glucosyl-glycolic acid benzylester are dissolved in 40 ml of ethanol/water 1/1 (v/v), and mixed with 400 g of palladium/active charcoal 10%. Hydrogenation on "PARR-APPARATUS" at 50 PSI produces the title compound, which is isolated in crystalline form after filtration and concentration under vacuum. $[\alpha]_D^{20}=-35.5°$ (c=1.03 in MeOH)

c)

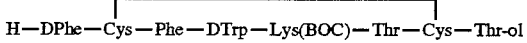

To a solution of 81 mg of tetra-O-acetyl-O-β-D-glucosyl-glycolic acid, 225 mg of

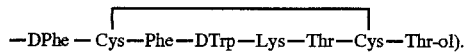

and 45 mg of HOBT in 2 ml of DMF, cooled to −30° C., are added 45 mg of DCCI, dissolved in 1 ml of DMF. After 48 hours and after thawing to room temperature, the resultant dicyclohexylurea is filtered off, and the title compound is precipitated from the filtrate by adding 20 ml of diisopropylether.

The following compounds were also produced analogously to example 24 (in these, SMS denotes the radical

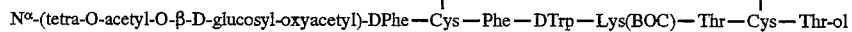

EXAMPLE 25
N$^\alpha$-(O-β-D-galactosyl-oxyacetyl)-SMS
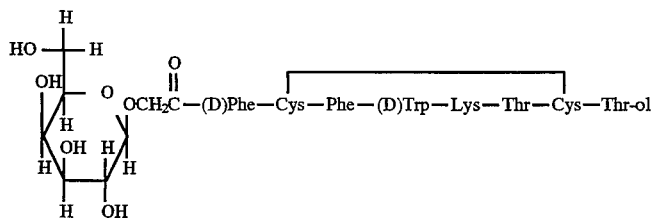
$[\alpha]_D^{20}$=–37.5° (c=1 in 95% AcOH) F: 0.95
EXAMPLE 26
N$^\alpha$-(O-β-cellobiosyl-oxyacetyl)-SMS
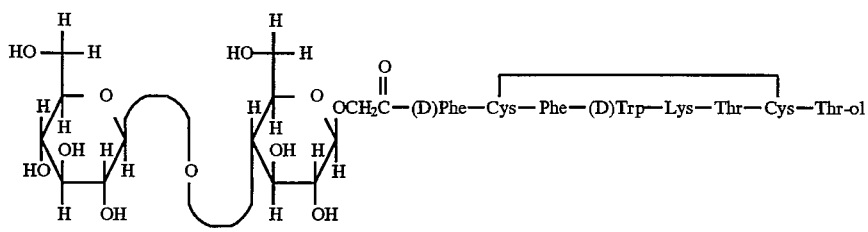
$[\alpha]_D^{20}$=–32.5° (c=1 in 95% AcOH) F: 0.91
EXAMPLE 27
N$^\alpha$-(O-β-(D)-glucosyl-oxyisobutyryl)-SMS
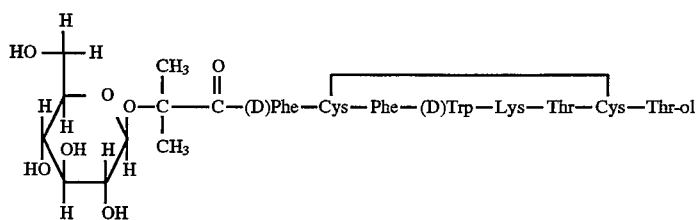
$[\alpha]_D^{20}$=–32.9° (c=1 in 95% AcOH) F: 0.93
EXAMPLE 28
N$^\alpha$-(O-α-(D)-glucosyl-s-(L)-oxyisovaleryl)-SMS
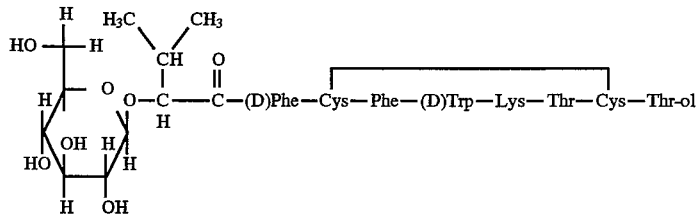
$[\alpha]_D^{20}$=–44.3° (c=1 in 95% AcOH) F: 1.00

EXAMPLE 29

[N-acetylmuramyl-(D)Phe¹]-SMS

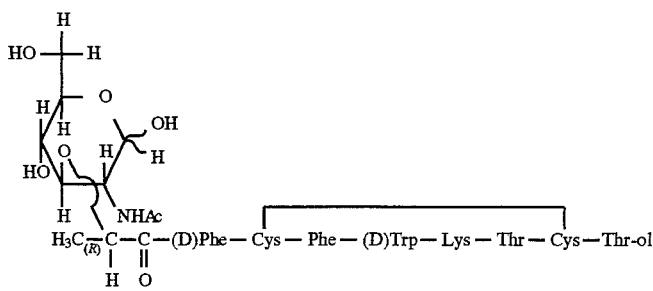

$[\alpha]_D^{20} = -15.4°$ (c=0.13 in 95% AcOH) F: 0.9

EXAMPLE 30

β-D-Glucosyl-thiocarbamyl-SMS

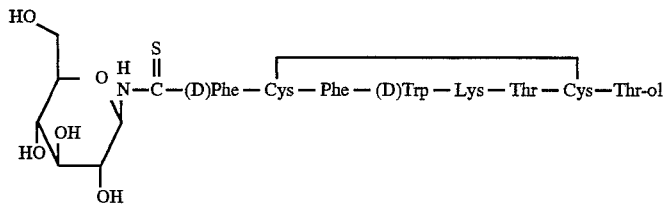

620 mg E-Fmoc-SMS in 50 ml CH₃CN/H₂O 3:] are treated with 0.45 ml triethylamine. 272 mg 2,3,4,6-tetra-O-acetyl-β-D-glucosyl-isothiocyanat are added and the mixture maintained at room temperature for 1 hour. The mixture is evaporated in a vacuum and the residue is taken up in a little methanol and treated with diisopropylether where: upon the product precipitate in practically pure form.

To split off the Fmoc group and the acyl group, the product in 50 ml absolute methanol is treated with a catalytic quality of IN NaOCH₃ in methanol. After 30 minutes time the reaction had been completed (by tlc), the mixture is neutralized with 1% acetic acid and evaporated in a vacuum.

The residue is taken up in water and extracted with ethyl acetate. The aqueous phase is lyophilized. The residue is purified over silica gel and desmineralized over e.g. Duolite. The title compound is obtained as a lyophilisate. $[\alpha]_D^{20} = -48.5°$ (c=1, 95% AcOH) F=1

The starting material E-Fmoc-SMS may be produced as follows:

5 g SMS acetate and 5 g NaHCO₃ in 100 ml DMF/H₂O 3:1 are treated with 1.6 g Fmoc-HOSu. After an hour at room temperature, the mixture is diluted with 400 ml H₂O and extracted with 250 ml ethyl acetate/methanol 95:5. The organic phase is dried with Na₂SO₄ and concentrated. After column chromatography over silica gel the starting material is obtained as an amorphous substance. $[\alpha]_D^{20} = 24.3°$ (c=1.13 DMF)

The following products may be obtained in analogous manner to that described in Example 30.

EXAMPLE 31

Cellobiosylthiocarbamyl-SMS

Starting from octa-acetyl-cellobiosyl-isothiocyanate

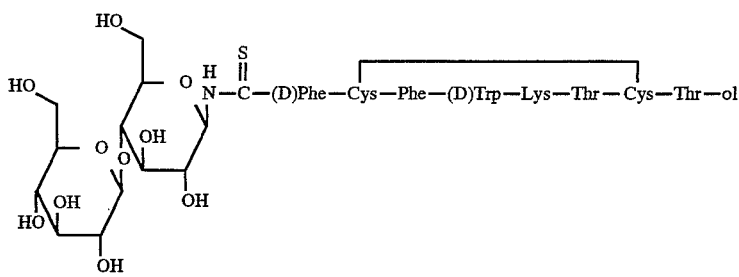

$[\alpha]_D^{20}$: -4.3° (c=1 in AcOH) F=0.87

EXAMPLE 32

β-D-Glucosylcarbamoyl-SMS

Starting from 2,3,4,6-tetra-O-acetyl-β-D-glucosyl-isocyanate

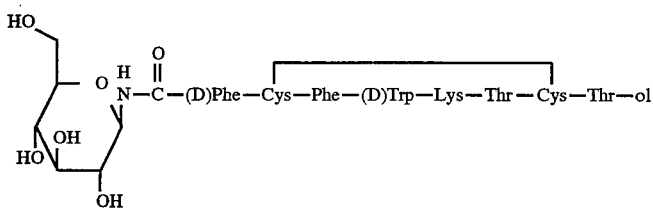

$[\alpha]_D^{20}$: −39.9 (c=1 in 95% AcOH) F=0.81

EXAMPLE 33

Cellobiosylcarbamoyl-SMS

Starting from octa-acetyl-cellobiosyl-isocyanate

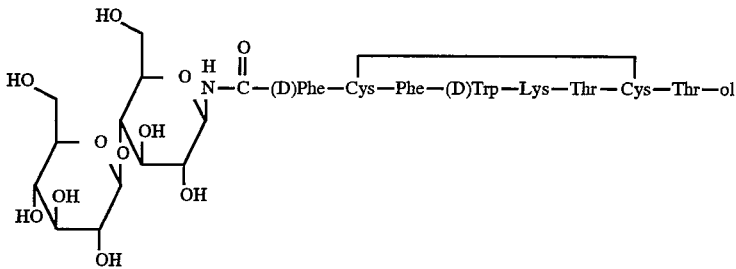

$[\alpha]_D^{20}$=−37.9° (c=1 in 95% AcOH) F=0.85

EXAMPLE 34

1-Deoxy-D-sorbityl-SMS

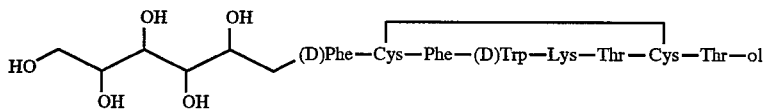

0.5 mg of the title compound of example 1 in 50 ml methanol is treated first with NaBH$_4$, then 5% acetic acid under conditions such that the pH does not increase beyond 7. Total use of NaBH$_4$ is about 10 equivalents.

After the complete reaction has occurred (4–5 hours) the mixture is treated with acetic acid to destroy excess NaBH$_4$. The mixture is concentrated under a vacuum. The residue is desmineralized with e.g. Duolite and purified over silica gel. The main compound besides 1-desoxy-D-mannityl-SMS is the title compound which is produced as a lyophilisate.
$[\alpha]_D^{20}$=−17.6° (c=1 in 95% AcOH) F=0.82

EXAMPLE 35

α-D-glucosyl(1–4)deoxysorbityl-SMS

In analogous manner to that described in Example 34 starting from the title compound of Example 2 the following compound is produced

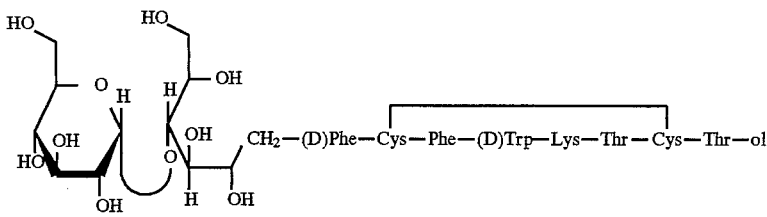

$[\alpha]_D^{20}=+1.6°$ (c=1 in AcOH) F=0.9

EXAMPLE 36

1,2-dideoxy-sorbityl-SMS

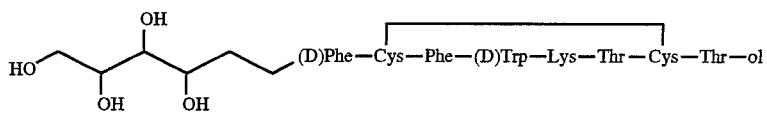

0.55 g Boc-SMS in 30 ml dioxane /H$_2$O 3:7 are treated with 50 mg NaBH$_3$CN. 250 mg 2-deoxy-D-glucose are added. The pH of the mixture is adjusted to 7 with: 0.1 ml HCl and heated to 100° C. for 6 hours. The mixture is cooled, freezed and lyophilized. The residue is taken up in ethyl acetate (50 ml) and shaken with water. The organic phase is dried and evaporated in a vacuum. The Boc group is split off in conventional manner with TFA. The product is purified over silica gel and desmineralized e.g. over Duolite to give the title compound. $[\alpha]_D^{20}=25°$ (c=1.95% HOAc) F=0.83

In analogous manner compounds of the foregoing examples 34 (starting from glucose) and 35 (starting from maltose) may be produced.

EXAMPLE 37

N$^\alpha$-isocaproyl-des(1–4)-[Ala$^7$,N$\epsilon$-(1-deoxyfructosyl)-Lys$^{11,18}$]salmon Calcitonin

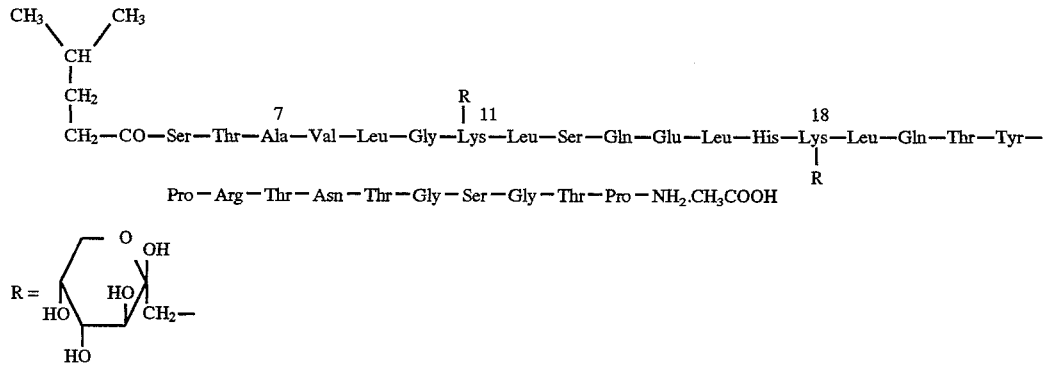

10.3 g of N$^\alpha$-isocaproyl-des(1–4)-[Ala$^7$]salmon calcitonin polyacetate and 1o8 g of D(+)-glucose are dissolved in a mixture of g4 ml of DMF and 6 ml of acetic acid. After 2 hours at 50° C., the product is completely precipitated by adding ether, then filtered off by suction, washed with ether and vacuum-dried. Purification is effected by dissolving ca. 5–10 g of the product in water, adding the solution to a reversed-phase column 4×25 cm, C-18 on silica-gel and chromatographing with a gradient of water and 0–80% of a solvent mixture comprising 38 parts of water, 60 parts of acetonitrile and 2 parts of 85% phosphoric acid. The fractions which contain the pure product are combined, filtered over a column of ca. 100 ml of a slightly basic ion exchanger in acetate form and washed with water. The filtrate is lyophilised and the title compound is obtained as the polyacetate, polyhydrate. $[\alpha]_D^{20}=-34.8°$ (c=0.73 in CH$_3$COOH 95%) F: 0.93 FAB mass spectroscopy 3407 (MH$^+$)

The N$^\alpha$-isocaproyl-Ser-Thr-Ala-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro-NH$_2$ used as the starting product may be produced as follows:

a) N$^\alpha$-isocaproyl-Ser(Bu$^t$)-Thr(Bu$^t$)-Ala-Val-Leu-OCH$_2$-phenyl-(p)OCH$_2$-co-(polystyrene-1%-divinylbenzene)

1 g of p-hydroxymethyl-phenoxymethyl-co(polystyrene-1%-divinylbenzene) is left to swell in dimethylformamide/methylene chloride 1:4 (v/v), filtered off by suction and mixed with a solution of 0.74 g of Fmoc-leucine and 0.19 g of i-hydroxybenzotriazole in 5 ml of the above-mentioned solvent mixture. 0.43 g of dlcyclohexylcarbodiimide and 85 mg of 4-dimethylaminopyridine, each in 5 ml of the same solvent mixture, are added whilst stirring. The mixture is stirred for 16 hours at 20°, filtered off by suction and washed with the solvent mixture, then with dimethylformamide. Fmoc-Leu-OCH$_2$-phenyl-(p)-OCH$_2$-co(polystyrene-1%-divinylbenzene) is obtained.

The N$^\alpha$-Fmoc group is split from the Fmoc-Leu-OCH$_2$-phenyl-(p)OCH$_2$-co(polystyrene-1%-divinylbenzene) (1.56 g corresponding to 0.7 mMol) by treating with piperidine (20% v/v) in DMF for 10 minutes. This is washed well with DMF, and then 0.71 g of Fmoc-Val-OH, 0.28 g of 1-hydroxybenzotriazole and 0.32 ml of diisopropylcarbodiimide, each dissolved in 5 ml of DMF, are added. After 45 minutes, the mixture is filtered by suction, and the peptide resin is washed well with DMF. The splitting of the $N^\alpha$-Fmoc group is repeated, as well as the coupling with the amino acid following in sequence, in the order given: Fmoc-Ala-OH (0.65 g) Fmoc-Thr(Bu$^t$)-OH (0.83 g), and Fmoc-Ser(Bu$^t$)-OH (0.80 g). In the latter reaction cycle (splitting of the Fmoc protecting group, acylation with protected amino acid) the amino acid derivative is replaced by isocaproic acid (0.41 g), the quantity of 1-hydroxy-benzotriazole is increased to 0.53 g and that of diisopropylcarbodiimide to 0.54 g, and coupling is effected for 15 hours. The protected peptide resin is washed well with DMF and methylene chloride, vacuum-dried at 40° C. for 15 hours, and the protected peptide resin is obtained as a colourless powder.

0.50 g of the partly protected peptide of stage c) are dissolved in a mixture of trifluoroacetic acid (50% v/v) and methylene chloride. After 1 hour, 50 ml of ether which contains 0.6 mMol of HCl is added. The mixture is filtered, washed with ether and vacuum-dried. The product is purified by "reversed-phase" chromatography in a gradient of acetonitrile in $H_3PO_4$ (2%). The combined fractions containing the pure substance are filtered over a basic ion exchanger in acetate form. The filtrate is lyophilised and the title compound is obtained as the polyacetate, polyhydrate. $[\alpha]_D^{20}=-32.2°$ (c=0.3 in AcOH 95%) F=0.87

EXAMPLE 38

$N^\alpha$-isocaproyl-des-(1–4)-[Ala$^7$, $N^\kappa$-($\alpha$-D-glucosyl-(1–4)-deoxyfructosyl)-Lys$^{11,18}$]salmon Calcitonin

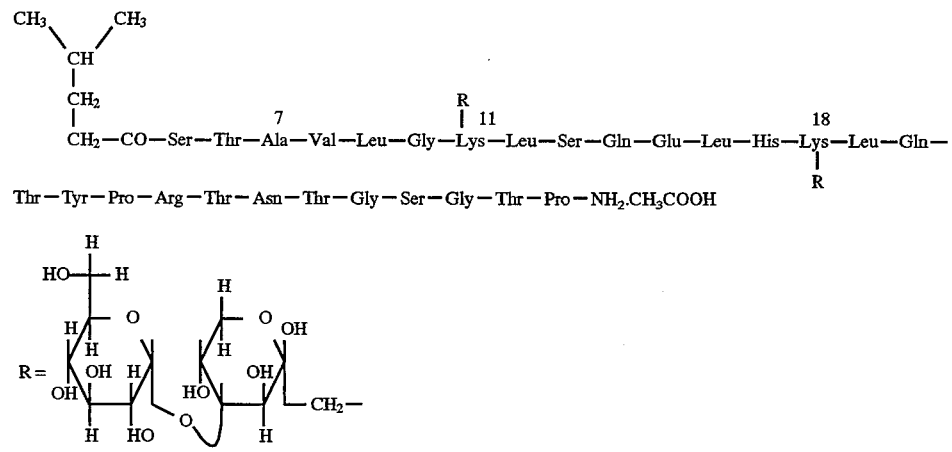

b) $N^\alpha$-isocaproyl-Ser-Thr-Ala-Val$^{-Leu-OH}$ $N^\alpha$-isocaproyl-Ser(Bu$^t$)-Thr(Bu$^t$)-Ala-Val-Leu-OCH$_2$-phenyl-(p)OCH$_2$-co(polystyrene-1%-divinylbenzene) (1.0 g) is stirred in a mixture of trifluoroacetic acid (5 ml) and methylene chloride (5 ml). The product is filtered, washed with the same mixture (5 ml), then with methylene chloride, greatly concentrated under vacuum, and totally precipitated by adding ether. The deposit is washed well with ether, dried under vacuum over solid potassium hydroxide, and the title compound is obtained as a colourless, amorphous powder.

c) $N^\alpha$-isocaproyl-Ser-Thr-Ala-Val-Leu-Gly-Lys(Boc)-Leu-Ser-Gln-Glu(OBu$^t$)-Leu-His-Lys(Boc)-Leu-Gln-Thr-Tyr-Pro-Arg-Thr-Asn-Thr-Gly-Ser-Gly-Thr-Pro-NH$_2$ To a solution of $N^\alpha$-isocaproyl-Ser-Thr-Ala-Val-Leu-OH (0.165 g) in DMF (7 ml) are added H-Gly-Lys(Boc)-Leu-Ser-Gln-Glu(OBu$^t$)-Leu-His-Lys(Boc)-Leu-Gln-Thr-Tyr-pro-Arg-Thr-Asn-Thr-Gly-Ser-Gly-Thr-Pro-NH$_2$ hydrochloride (0.59 g), 3,4-dihydro-3-hydroxy-4-oxo-1,2,3-benzotriazine (0.017 g), dicyclohexylcarbodiimide (0.065 g) and sufficient N-ethyl-N,N-diisopropylamine for a sample of the reaction mixture on moistened pH paper to indicate a reaction of ca. pH 6. After 16 hours, the mixture is precipitated by adding ether, dried, and the title compound is obtained.

d) $N^\alpha$-isocaproyl-Ser-Thr-Ala-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro-NH$_2$ The corresponding di-$N^\varepsilon$-maltulosyl derivative is produced analogously to example 37 using D(+)-maltose monohydrate instead of D (+)-glucose. The reaction time at 50° C. is lengthened to 15 hours. Isolation and purification are identical and the title compound is obtained as the polyacetate, polyhydrate, FAB mass spectroscopy: 3730.9 (MH$^+$) $[\alpha]_D^{20}=-1.52°$ (c=0.16 in 95% AcOH) F=0.97 Analogously to example 37 the following compounds Ire prepared:

EXAMPLE 39

$N^\alpha$-isocaproyl-[$N^\epsilon$-(1-deoxyfructosyl)-Lys$^7$]-salmon Calcitonin [5–32)amide

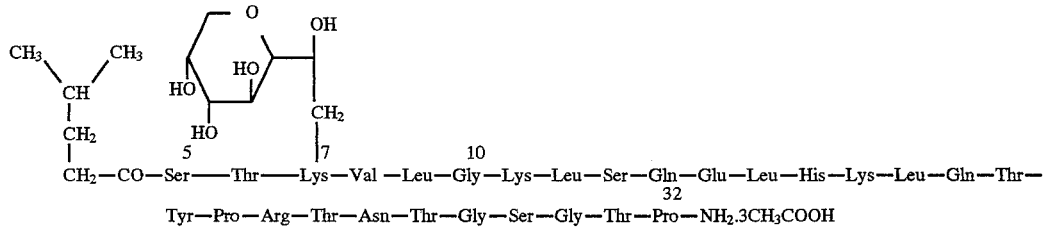

$[\alpha]_D^{20}$=–40.0° (c=0.27 in AcOH 95%) F=0.84

EXAMPLE 40

$N^\alpha$,Lys$^{11}$-$N^\epsilon$,Lys$^{18}$$N^\epsilon$-tris-(1-deoxyfructosyl)-salmon Calcitonin

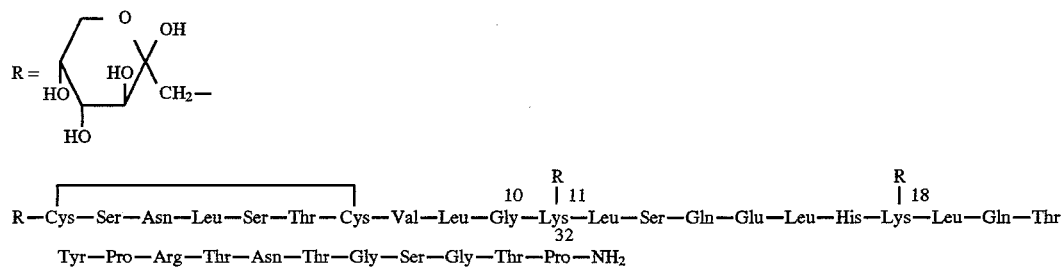

$[\alpha]_D^{20}$=–5.3° (c=0.38 in AcOH 95%) F=0.75

EXAMPLE 41

$N^\alpha$-isocaproyl-des(1–4)-[$N^\epsilon$-(1-deoxyfructosyl)-Lys$^{7,11,18}$]salmon Calcitonin-(5–32)amide

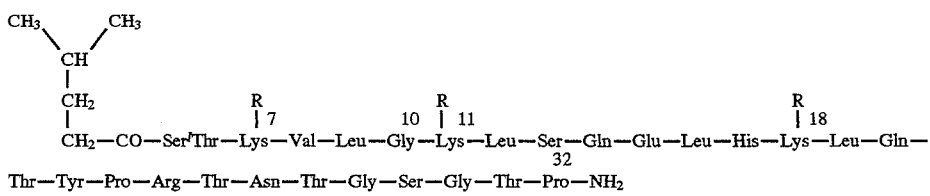

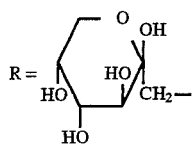

$[\alpha]_D^{20}$=–37.4° (c=0.155 in 95% AcOH) F=0.84

EXAMPLE 42

N$^\alpha$-quinoyl-[Ala$^7$]salmon Calcitonin-(5-32)-amide

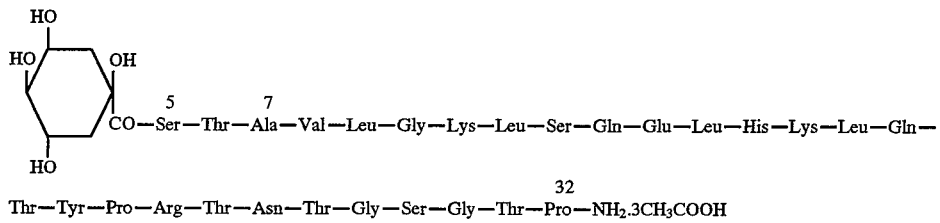

Thr—Tyr—Pro—Arg—Thr—Asn—Thr—Gly—Ser—Gly—Thr—Pro—NH$_2$.3CH$_3$COOH

The title compound was produced analogously to example 21. $[\alpha]_D^{20}=-35.7°$ (c=0.37 in AcOH 95%) F: 0.88

EXAMPLE 43

N$^\alpha$-quinoyl-[Ala$^7$]salmon Calcitonin-(4-32)-amide

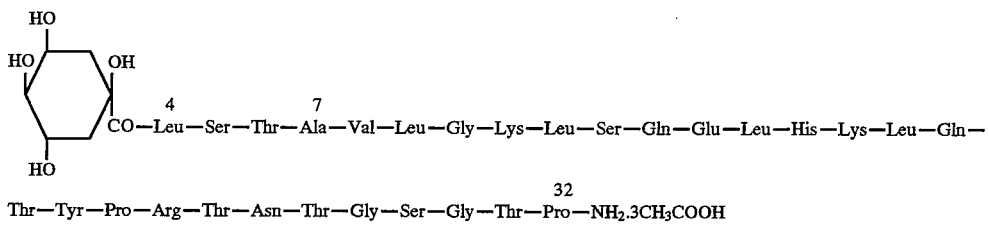

Thr—Tyr—Pro—Arg—Thr—Asn—Thr—Gly—Ser—Gly—Thr—Pro—NH$_2$.3CH$_3$COOH

The title compound was produced analogously to example 21. $[\alpha]_{20}^D=-39.3°$ (c=0.29 in 95% AcOH) F: 0.89

The starting peptides [Ala$^7$]-salmon calcitonin-[5-32]-amide and [Ala$^7$]-salmon calcitonin-(4-32)-amide required for examples 42 and 43 may be produced analogously to the starting material of example 37.

EXAMPLE 44

[N-deoxy-fructosyl-Cys$^1$]-oxytocin

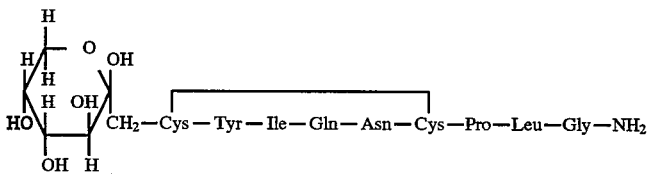

0.5 g of D(+)-glucose and 0.5 g of oxytocin are dissolved in 50 ml of MeOH/HOAc 9/1 and kept at 65° C. for 3 hours, The solution is then concentrated by evaporation, chromatographed over silica gel and freed from salt over Duolite (H$_2$O/ethanol/HOAc gradient). A white lyophilisate is obtained. $[\alpha]_D^{20}=-23°$ (c=0.32 in 95% HOAc) F: 0.95

EXAMPLE 45

Ac-(D)-Phe(4-Cl)-(D)Phe(4-Cl)-(D)Trp-Ser-Tyr-

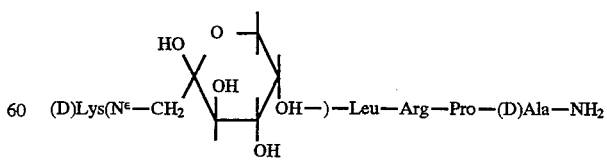

60 mg of Ac-(D)Phe(4-Cl)-(D)Phe(4-Cl)-(D)Trp-Ser-Tyr-(D)-Lys-Leu-Arg-Pro-(D)Ala-NH$_2$ and 72 mg of D(+) glucose are dissolved in a mixture of 10 ml of MeOH and 1 ml of AcOH, and stirred for ca. 20 hours at 60° C. The product is precipitated with ether and centrifuged off. The residue is dissolved in ca. 100 ml of $H_2O$, and the pH is adjusted to 8 with dilute NaOH. The product is adsorbed on a column of Duolite ES 861 and eluted with a gradient of $H_2O \to$dioxane-$H_2O$-AcOH (60:40:3). Fractions containing the desired product are concentrated under vacuum, then lyophilised. The title compound is obtained. $[\alpha]_D^{20}=-25°$ (c=0.5 in 95% AcOH) F: 0.83

EXAMPLE 46

$N^{\alpha A1}, N^{\alpha B1}, N^{\epsilon B29}$-tris(1-deoxyfructosyl)-porcine-Insulin A suspension of 1 g (0.17 mmol) and 0.47 g (2.6 mmol) glucose in 10 ml dimethylformamide/acetic acid 9:1 are stirred for 1 hour at 60° C. The solvent is removed at 30° C. in a high vacuum. The residue is dissolved in 300 ml $H_2O$, adjusted to pH 7 and the mixture passed through a small desmineralising column (Duolite ES 861 2.5×15 cm). The glucose is eluted with water and the peptide by isopropanol/water ethyl acetate 59:39:2.

The solvent is removed and the mixture lyophilised. The residue is taken up in 300 ml water and purified through reversed phase chromatography.

(2×25 cm column, RP 18, 10 nm, Buffer 57 mmol $NaClO_4$, 20 mmol triethylamine, 8.4 mmol phosphoric acid, pH 3 with 4N NaOH, Gradient 0–65% A-B.

Buffer A   Buffer pH 3/acetonitrile 9:1
Buffer B   Buffer pH 3/acetonitrile 4:6

The fractions containing the heading compound are collected, combined, concentrated, diluted with 300 ml water and passed through a desmineralising column as described above. Salts are eluted with water. The peptide is eluted with isopropanol/water/ethyl acetate 59:39:2. The appropriate fractions are combined and concentrated to give the heading compound. $[\alpha]_D^{20}=56.3°$ (c=0.5 AcOH) F=0.88.

EXAMPLE 47

$N^\alpha,Lys^{12}$-$N^\epsilon,Lys^{21}$-$N^\epsilon$-tris-(1-deoxyfructosyl)-(D[Ala$^2$]-hpGRF-(1–29)-NH$_2$

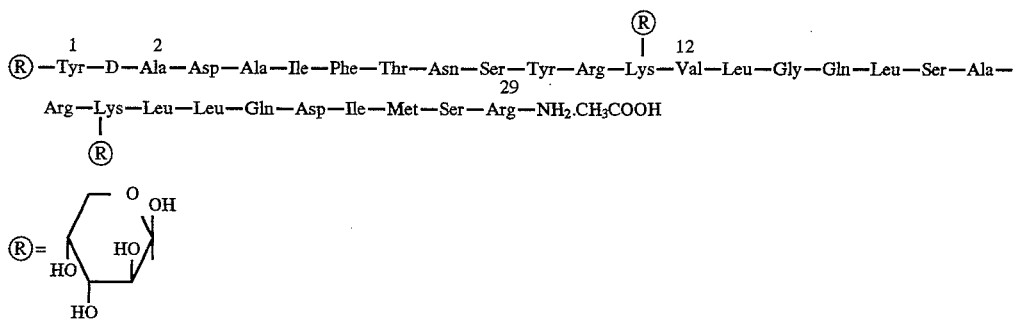

In analogous manner to example 37 starting from (DAla$^2$] hpGRF—the title compound is produced. $[\alpha]_D^{20}=-5.6°$ (c=0.2 in 95% AcOH) F=0.82

EXAMPLE 48

$N^\alpha, N^\epsilon$-bis(1-deoxyfructosyl)Lys-vasopressin

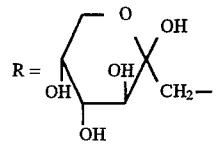

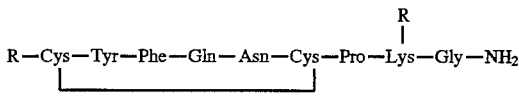

A suspension of 118 mg (0.1 mmol) Lys$^8$-vasopressin and 360 mg (2 mmol) glucose in 5 ml methanol/ethyl acetate 9:1 are stirred at 65° for 2 to 4 hours. The solvent is removed under a vacuum. The residue is taken up in 30 ml water and the solution lyophilised. To remove the excess glucose the peptide (solution in 40 ml water at pH 7.3) is adsorbed on a Duolite column (1.5×10 cm). The glucose is eluted with water and the peptide with a mixture of isopropyl/water/ethyl acetate 59:39:2. The mixture is purified on a silica gel column (eluant chloroform/methanol/ethyl acetate/water 7:4:1:1).

The fractions containing the heading compound, are concentrated and lyophilised to give the title compound. $[\alpha]_D^{20}=-52°$ (c=0.5 in 95% HOAC) F=0.84.

EXAMPLE 49

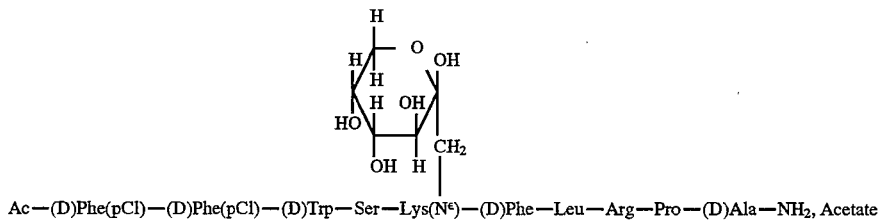

Ac—(D)Phe(pCl)—(D)Phe(pCl)—(D)Trp—Ser—Lys(N$^\epsilon$)—(D)Phe—Leu—Arg—Pro—(D)Ala—NH$_2$, Acetate The title compound is produced in analogous manner to example 45 starting from Ac-(D)Phe(pCl)-(D)Phe(pCl)-(D)-Trp-Ser-Lys-(D)Phe-Leu-Arg-Pro(D)Ala-NH$_2$, acetate and D(+)glucose. $[\alpha]_D^{20}=-36°$ (c=0.5 in 95% AcOH) F=0.86

EXAMPLE 50

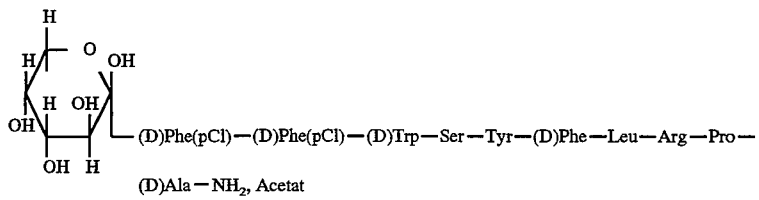

(D)Ala—NH$_2$, Acetat

The title compound is produced in analogous manner to example 45 starting from H-(D)Phe(pCl)-(D)Phe(pCl)-(D)-Trp-Ser-Tyr-(D)Phe-Leu-Arg-Pro-(D)Ala-NH$_2$, acetate and D(+)glucose. $[\alpha]_D^{20}=-32°$ (c=0.5 in 95% AcOH) F=0.94

EXAMPLE 51

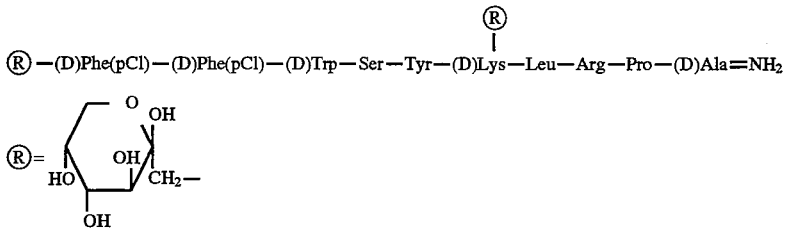

200 mg H-(D)Phe(pCl)-(D)Phe(pCl)-(D)Trp-Ser-Tyr-(D)Lys-Leu-Arg-Pro-(D)Ala-NH$_2$ and 520 mg D(+)glucose in DMF/AcOH 15:1 are stirred at 60° C. for 3 hours. The mixture is concentrated in a vacuum, precipitated with ether, filtered and dried.

The residue is purified as follows:

1) Adsorption on Duolite ES 861 and elution with a mixture of dioxan-H$_2$O-AcOH.
2) Column chromatography on silica gel using as eluant CHCl$_3$/AcOH/H$_2$O.
3) Preparative HPLC ("Reversed phase") chromatography on an octadecyl-silica gel column. Elution with an acetonitrile gradient in 2% H$_3$PO$_4$.

Fractions which contain the heading compound are combined, filtered through a column containing a weakly basic ion exchanger in acetate form, concentrated and lyophilised to give the title compound. $[\alpha]_D^{20}=-22.6°$ (c=0.5 in 95% AcOH) F=0.63

The synthesis of the invention may be effected as follows:

EXAMPLE S1

Production of Octreotide (=SMS)

1) Production of acetal anchor (N-CF$_3$CO-Threoninol acetal of p-formylphenoxy-acetic acid).

105 g (1.0 mmol) L-Threoninol is added to 200 ml methanol which is stirred by a stream of nitrogen. A clear solution results. A solution of 200 ml trifluoro acetic acid methyl ester in 250 ml methanol is added to the mixture at 0°. The mixture is maintained at a temperature of about 10° C. by cooling with an ice bath.

After 1.5 hours no more free Threoninol is detectable in the mixture. Concentration at 40° C. gives a white crystalline residue.

The residue is dissolved in 200 ml ethyl acetate at 70° C. and precipitated by the addition of hexane. The mixture is cooled to 0° C., washed with hexane and dried at room temperature. N-trifluoroacetyl threoninol results.

50.3 g (0.25 mol) of the resultant product is dissolved in 1.25 liters tetrahydrofuran and 75 ml of tri methylchlorosilane is added dropwise. Immediately thereafter a mixture of 70 ml triethylamine and 250 ml tetrahydrofuran is added. A white suspension results which is stirred for 4 hours. The mixture is filtered and the filtrate evaporated at 40° C. to give an oil.

The oil is dissolved in 1.5 liters of methylene chloride and treated with portions of 90.4 g p-formyl-phenoxyacetic acid at room temperature. Portions of 9 ml trifluoromethanesulphonic acid trimethylsilyl ester are added. The mixture is stirred for 24 hours at room temperature, then filtered and the residue is washed well with methylene chloride.

The filtrate is concentrated at 40° C. to give an orange red resinous product. This product is chromatographed over silica gel. Elution is effected with ethyl acetate. On concentration of the relevant fractions the heading compound is obtained with a purity of 97% (HPLC).

2) Building up of the protected octa-peptide 17.2 g aminomethylated polystyrene (Brand Dow 0.7% by weight of N corresponding to 0.5 mmol amino-methyl groups per g resin) are suspended in 80 ml methylene chloride/DMF 4:1. Successively there are added 4.17 g of the end product of step 1, 1.6 g HOBT and 4.0 g DCCI. After the mixture is stirred for 2 hours at room temperature, the Kaiser test is negative. The mixture is filtered and washed.

The washed resin is suspended in 100. ml tetrahydrofuran and methanol 3:1 and treated with portions of 10.4 g sodium borohydride. The mixture is stirred for 6 hours at room temperature, filtered and the resin washed. The resin is suspended in methylene chloride/DMF 4:1. 5.5 g Fmoc-Cys (S-t-Bu)OH, 1.74 g HOBT and 3.6 g DCCI are added. The Fmoc protecting group is split off with piperidine (2×20 minutes contact time).

In analogous manner in successive cycles the following N-Fmoc protected amino acids are coupled using HOBT/DCCI-ThrOH; Lys (BOC)-OH: D-TrPOH, Phe-OH, Cys(S-tBtu)OH and D-Phe-OH to-give the Fmoc protected octapeptide resin. Final loading 0.26 mmol/g.

3) Oxidation and splitting off

The resultant resin is suspended in 100 ml trifluoroethanol/methylene chloride 1:1 and treated with 50 ml tributylphosphine. The mixture is stirred for 70 hours at room temperature. The mixture is filtered, washed and treated with a 100 ml 1:1 mixture of tetrahydrofuran and 1N aminoacetate solution. 1.1 ml of 30% aqueous hydrogen peroxide are added. The mixture is stirred for 24 hours at room temperature. The resin is washed. The mixture is treated with 20 ml trifluoroacetic acid, 80 ml methylene chloride, 10 ml water, and ml thioanisole. The mixture is stirred for 2 hours, then filtered and washed with trifluoroacetic acid and methylene chloride. 200 ml diethyl ether are added to the filtrate. The resultant precipitate is filtered off. The residue is dissolved in aqueous buffer and demineralised, e.g. using Duolite. The solution is freeze-dried as the acetate to give the title compound as the acetate. All the above examples, e.g. the compounds of examples 1 and 2 may be produced in analogous manner.

EXAMPLE S2

Production of $N^\alpha$-[α-glucosyl(1–4)-deoxyfructosyl]-SMS (see Example 2)

393 g of the octapeptide bonded to the resin are produced according to the above example S2. The cysteine protecting groups are removed reductively. The peptide bond to the resin is oxidized to the cyclic octapeptide by hydrogen peroxide in a mixture of tetrahydrofuran/water.

After washing in tetrahydrofuran and then DMF the peptide resin is shaken in 3600 ml of a mixture of DMF/ACOH.(8:1) The suspension is treated with 526 g D(+) maltose monohydrate. The mixture is warmed to 60° and stirred for 18 hours at this temperature.

The mixture is cooled and the peptide resin filtered off, and successively washed with DMF and methanol. Then it is washed with methylene chloride. The peptide is then split over 1 hour from the resin with a mixture of 2900 ml methylene chloride and 716 ml trifluoroacetic acid with a trace of water.

The filtrate is then stirred and treated with portions of 597 g sodium carbonate, stirred for 30 minutes and filtered. The residue is washed with methylene chloride and methanol.

The filtrate is concentrated to dryness.

It is demineralised using an unfunctionalized polystyrene column like Duolite, or reversed phase HPLC material such as silica gel treated with silicone and bearing long chain fatty alcohol groups (e.g. Labomatic, Switzerland, Brand HB-SIL-18-20-100). The pure title compound is obtained.

The compounds of the invention exhibit pharmacological activity and are therefore indicated for use as pharmaceuticals for therapy.

The activity of the compounds of the invention may be observed in standard pharmaceutical and biopharmaceutical tests. The compounds are in general at least as potent as the unmodified peptide (i.e. the corresponding sugar free peptide) on administration by injection or orally. They are in general better absorbed, are more easily soluble in water, and have a longer duration of action.

The compounds of the invention are therefore useful in the same indications as for the unmodified peptides.

The compounds of the invention may be compared with the unmodified peptides in standard bioavailability tests.

The compounds of the invention, for example, may be detected in the blood plasma for a longer period after administration than the unmodified peptides, as indicated in standard bioavailability experiments.

The compounds of the invention and the unmodified peptide may be administered to for example dogs in a single dose sufficient to produce a therapeutic effect by oral or intravenous administration.

Doses used are those which permit the peptide or a metabolite thereof to be detected in the blood. Detection may be effected in conventional manner, e.g. by radioimmunoassay.

In the above mentioned test, it has for example been determined that the example 2 compound produced on oral administration a ten fold higher blood concentration compared with octreotide.

The absolute bioavalability of orally and intravenously administered example 2 compound, measured on the basis of the AUC (area under the curve) is 5 times higher than that of octreotide. The elimination half-life on intravenous administration is about 2.3 hours compared with about 0.5 hour for octreotide.

Additionally the compounds of the invention advantageously are eliminated to a greater extent through the kidneys. This may be observed in standard tests.

Fasted Male rats (225–375 g) are administered orally with water (50 ml/kg). After 30 minutes the animals are anaesthetized with e.g. Inactin (100 mg/kg i.p.). The bile duct and bladder are cannulated. Both V. jugularis are exposed. In one vein an infusion of glucose 5% with ethanol 1% is administered (5 ml/hr) to stimulate diuresis. The other vein is used to take blood samples (0.5 ml) every hour over 4 hours.

The compound of the invention and the unmodified peptide is administered s.c. at a dose of from about 10 to about 1000 microgram/Kg. The concentration of the compound is determined in conventional manner e.g. by RIA.

In the above test for example the following results have been obtained with the example 2 compound and octreotide at a dose of 10 microgram/kg:

|  | Percentage eliminated through | |
|---|---|---|
|  | Bile | Urine |
| Example 2 compound | 1.6 | 36 |
| Octreotide | 22 | 19 |

Whereas octreotide is eliminated in both the bile and urine the example 2 compound is predominantly eliminated in the urine.

Improved absorption on oral administration may be detected for the compounds of the invention as follows:

The compound of the invention and the unmodified analogue are administered orally to OFA rats (e.g. 10 mg/kg). After definite periods of time, e.g. 15, 30 and 60 minutes, blood samples are collected, These are analysed for their drug content by e.g. RIA.

It has for example been determined in this test that the compound of example 44 at a dose of 10 mg/kg exhibits a 50 to 100 per cent higher absorption than the unmodified peptide, oxytocin. Results are as follows:

TABLE

| Rat plasma levels following oral administration. Results given in ng/ml | | | |
|---|---|---|---|
|  | 15 mins. | 30 mins. | 60 mins. |
| oxytocin | 7.53 | 3.60 | 2.55 |
| compound of example 44 | 11.79 | 6.98 | 3.98 |

The pharmacological activities of the compounds of the invention may be investigated in standard pharmacological tests, e.g. after injection, aid, if desired, compared with those of the unmodified peptides, e.g. in terms of potency and duration of action.

For example pharmacological tests may be effected to examine the effects of the compounds of the invention on hormones in animals. Thus the compounds which inhibit the secretion of hormones may be tested by measuring the lowering of blood levels of the hormone.

Compounds of the invention which inhibit GH (growth hormone) secretion, especially the compounds of formula VIII, and more especially compounds of formula VIII a to f, and reduce the GH concentrations in the blood, may be tested as follows:

Fasted rhesus monkeys (at least 5 monkeys) in primate chairs receive the compound of the invention in a piece of banana as vehicle. The compounds are administered at a dose of from about 0.1 mg/kg to about 10 mg/kg p.o.

Blood is taken from the V. Saphena via a catheter. The GH concentration in the blood is measured by RIA (radio immunoassay).

In this test with rhesus monkeys it has for example been determined that the example 2 compound at a dose of 0.1 mg/kg lowered the GH secretion by at least 50 per cent for longer than 10 hours, compared with a 5 hour duration of lowering effect with-the unchanged peptide, octreotide.

A further test is as follows:

Male rats are decapitated and blood is collected 1 hour after administering the GH secrection inhibiting compound in several logarithmically spaced doses. The GH level in the serum is determined means of RIA. In this test, these compounds of the invention are active at doses from about 0.02 to about 30 microgram/kg s.c.

In this test it has for example beer determined that the example 1,2,21 and 24 compounds have an $ID_{50}$ of 0.045, 0.190, 0.3 and 0.2 microgram/kg s.c. respectively compared with the $ID_{50}$ for natural stomatostatin in the same test of 93 microgram/kg s.c. (the $ID_{50}$ indicates the amount of compound required to lower the GH content by 50% compared with that of untreated control animals).

Unlike natural somatostin, the GH secretion inhibiting compounds of the invention are highly active in this test for a long period of time (e.g. 6 hours).

The GH-reducing activity of these compounds is also observed after oral application to male rats having oestradiol implants. In this test there are relatively small variations in the GH level, The test is carried out as follows:

A loop (length 50 mm Ø 3 mm) of silastic with 50 mg of oestradiol is implanted under ether anaesthesis under the dorsal skin of male rats which have a weight of ca. 300 g. At various times (1 to 6 months later), these animals are used repeatedly for tests. The test substance is administered either s.c. or orally.

Directly before, as well as at various times after administration of the substance, ca. 0.8 ml of blood is removed from the retro-orbital plexus. It is centrifuged and the GH level in the serum is determined by RIA.

The compounds of the invention are, after oral administration, more active than the corresponding unmodified peptides, even after several hours. The $ID_{50}$ for each of the compounds of examples 1 and 2 after two hours is ca. 17 to 40 times lower than that of the unmodified peptide octreotide. Further results are as follows:

| Compound of example | $ID_{50}$ p.o. microgram/kg |
|---|---|
| 21 | 500 |
| 24 | 25 |
| Octreotide | 1400 |

These compounds of the invention are useful for indications where an inhibition of GH secretion is desired. Indications include diabetes mellitus, the prevention and treatment of angiopathy and proliferative retinopathy, as well as acromegaly.

The GH secretion inhibiting compounds of the invention also inhibit pancreatic secretion.

This inhibition may be detected in tests on animals.

The method is described in Scand. J. Gastroint. 6, 423 (1975) by S. J. Konturek et al. may be used.

The GH secretion inhibiting compounds of the invention also inhibit gastric acid secretion and increase the pH of the stomach juices to higher pH units.

The activity of these compounds is observed in e.g. the following test:

GH secretion inhibiting compounds of the invention are administered to fasted rats with fistula implanted in their stomach in doses from about 0.05 mg/kg to about 5 mg/kg by stomach tune. After 1 hour the fistula is opened. The stomach Juice is collected in 30 minute periods. The collected volumes are registered and the acid concentration determined.

In the above mentioned test the compound of example 2 increased the pH to 6–8 for 3,5 hours. Octreotide increased the pH units to 6–7 for only 2 hours. The compound of example 2 is at least 60 times more active than cimetidine in this test system.

The GH secretion inhibiting compounds of the invention, especially the compounds of formula VIII are therefore useful in the treatment of gastro-intestinal disorders, e.g. in the treatment of peptic ulcers, gastro-intestinal bleeding, acute pancreatitis and gastro-enteropancreatic tumours (e.g. vipomas, insulinomas, glucagonomas, etc.).

The GH secretion inhibiting compounds of the invention also inhibit the proliferation and/or keratinisation of epidermal cells, and are therefore useful in the treatment of dermatological illnesses which are associated with pathological proliferation and/or keratinisation of epidermal cells, especially in the treatment of psoriasis.

Furthermore, these compounds are useful in the treatment of degenerative senile dementia, also the Alzheimer type (SDAT) of senile dementia, or in the treatment of cluster headaches. (repeated headaches).

For these indications, the appropriate dosage will, of course, vary depending upon, for example, the compound employed, the host, the mode of administration and the nature and severity of the condition being treated. However, in general, satisfactory results in animals are indicated to be obtained at daily dosages from about 0.005, e.g. 0.03, microgram/kg to about 300 microgram/kg animal body weight. In larger mammals, for example humans, an indicated daily dosage is in the range from about 2 micrograms to about 2 mg of a compound conveniently administered, for example, in divided doses up to four times a day.

The sugar derivatives of calcitonin and of calcitonin analogues or derivatives according to the invention, more especially the derivatives of formula X reduce the calcium plasma level. Moreover, they are functional antagonists of the parathormone, and effect a positive calcium balance in the bones. The hypocalcemic activity of the new compounds may be measured in known manner, e.g. according to the method of M. Azria et al., reported in the Calcitonin 1984 Symposium, 24th October, Milan and published as "Short Communication" in "Current Clinical Practice Series" No. 42, Excerpta Medica 1986, page 104. In this method, a $Ca^{2+}$-ion selective electrode is used, so that the content of calcium ions in the blood of young rabbits or dogs may be continuously measured. The compounds are administered i.v. at a dosage of from about 0.1 to about 10 micrograms/kg, e.g. conforming to ca. 1 international unit per kg. The measurements are carried out over 5 hours and the AUC "area under the curve" is calculated.

The compounds can also be tested in other tests, e.g. in the hypocalcemic standard test of M. Kumar et al., J. Endocrinology (1965), 33, page 46g., on rats in different dosages giving a hypocalcemic activity of 300 to 6000 international units per mg for the hypocalcemic compounds according to the invention.

It has for example been determined that each of the compounds of examples 37 and 38 have a duration of action that is much longer than with the unmodified peptide, when administered i.v. to dogs (5 µg/kg). In this test, after 3 hours a reduction in the calcium level in the blood of 15 to 18% was observed for compounds C and D; after 6 hours, a calcium reduction could no longer be detected for the unmodified peptide,; whereas after example 37 and 38 compounds, the reduction in the calcium level was still as pronounced as after 3 hours.

The hypocalcemic compounds of the invention are thus useful for all conditions in which a reduction of the plasma calcium level or an effect on bone metabolism is desired, e.g. hypercalcemia, a result of a deficiency in the endogenic thyrocalcitonin through a loss of thyroid tissue or hyperfunction of the parathyroid bland. They are also indicated for all bone conditions which are based on increased bone friability or in which a calcium fixation in the bone is desired, e.g. osteoporosis of various kinds (e.g. postclimacteric, posttraumatic, caused by corticosteroid therapy or by inactivity, malignant dieseases etc.), fractures, osteomalacia, rickets and renally-induced osteodystrophy, pain e.g. pain in the bones in connection with osteoporosis, neurodystropic illnesses, Paget's disease, and in combined therapy with calcium phosphate.

For these calcium-related indications, the appropriate dosage will, of course, vary depending upon, for example, the compound employed, the host, the mode of administration and the nature and severity of the condition being treated. In larger mammals, for example humans, an indicated parenteral daily dosage is in the range from about 5 to about 1500 IU of a compound conveniently administered, for example as a single dose or if desired every 2 to 3 days.

Compounds of the invention, which are sugar derivatives of LHRH or analogues thereof, inhibit lutenizing hormone secretion, e.g. as indicated by an inhibition of ovulation in animals.

This test is effected according to M. Marko and E. Flückiger, Experientia 30, 1174–1176 (1974):

Adult female rats of the Ivanovas Wistar strain (Sprague Dawley, Iva:SDIV, 200–250 g) are kept under standard conditions: 14 h light (from 04.00 to 18.00 hours); 24° C.; 55–60% rel.humidity; food and water ad libitum.

Animals with regular 4-day cycles are injected on proestrus day at 13.00 h with the compound, subcutaneously or by the oral route. The next day at 9.00 a.m. the rats are sacrified and ova counted on both Fallopian tubes with the aid of a dissecting microscope. Only when no eggs are found is ovulation considered to be inhibited. The mean number of eggs per ovulating rat in each treatment groups is also determined.

In general these compounds of the invention are effective in a range from about 0.0005 to about 10 mg/kg. For example the example 45 compound is active at 0.01 mg/kg s.c. The inhibiting effect on luteinizing hormone secretion of the compound can also be tested in vitro: Pituitary cell cultures are prepared according to the method of Vale (W. Vale and G. Grant: Methods in Enzymology 37, 82–93 (1975) as has been described previously (M. Marko and D. Romer: Life Sciences, 33, 233–240 (1983). Primary cultures are maintained for 4 days in an incubator at 37° C. Thereafter the cells are washed and incubated for 3 hours in 1 ml medium containing LHRH or the test compound. At the end of the incubation, the supernatant is removed and assayed for LH by specific radioimmunoassay.

In this test in general the test compounds are found to be effective in a range from about $10^{-12}$ to about $10^{-7}$M concentration, inhibiting the LHRH-induced LH secretion in a dose-dependent manner.

For these LHRH indications, the appropriate dosage will, of course, vary depending upon, for example, the compound employed, the host, the mode of administration and the nature and severity of the condition being treated. However, in general, satisfactory results in animals are indicated to be obtained at daily dosages from about 0.005 microgram/kg animal body weight. In larger mammals, for example humans, an indicated daily dosage is in the range from about 2 mg to about 20 mg of a compound conveniently administered, for example, in divided dosed up to four times a day.

For the example 2 compound-an indicated dose is from 3 to 10 mg three times a day, e.g. p.o. for diabetes or ulcers.

The compounds of the invention may be administered by any conventional route, for example enterally, e.g. orally, e.g. in the form of drinking solutions, tablets or capsules, nasally, e.g. in the form of liquid or powder sprays and ointments., or parenterally, e.g. in the form of injectable solutions or suspensions.

The appreciate dosage of the compounds of the invention for any particular route of administration, e.g. by nasal, or oral, may be ascertained by standard bioavailability trials using the same substance injected i.v., i.m., or s.c. In general for oral administration the daily doses are about 10 to about 100 times higher than that available for injection i.m. or s.c.

The compounds of the invention may be administered in any pharmaceutically acceptable form, e.g. in free form, e.g. free base form or, when the compound is an acid, in free acid form, or in pharmaceutically acceptable salt form. The salt form may be for example an acid addition salt form or when the compound is an acid in pharmaceutically acceptable cationic salt form. The compounds may also be administered in complex form. The compounds may additionally or alternatively be in the form of a solvate, e.g. a hydrate.

The compounds of the invention exhibit the same order of activity in each of these form.

The present invention also provides pharmaceutical compositions for a compound of the invention in pharmaceutically acceptable form in association with at least one pharmaceutical carrier or diluent. Such compositions may be manufactured in conventional manner.

Unit dosage forms of the invention contain 0.5 micrograms to 10 mg of the compounds, e.g. for the GH and LH indications.

A drink ampoule or injectable solution may contain per ml for example 8.5 mg of the example 2 compound in acetate form, 11.45 mg citric acid, 6.32 mg NaOH, 4.5 mg NaCl.

The present invention also provides a compound of the invention for use in any indication mentioned above, including lowering GH secretion, diabetes mellitus, reducing gastric secretions and acromegaly for the somatostatin like compounds of the invention.

The present invention also provides the use of a compound of the invention in the manufacture of a medicament suitable for use in the treatment of any indication mentioned above, including lowering GH secretion, diabetes mellitus, reducing gastric secretions and acromegaly for the somatostatin like compounds of the invention.

We claim:

1. In a process for the production of a biologically active peptide alcohol of the formula $$Y-CO-NH-\underset{\underset{CH_2-OH}{|}}{\overset{\overset{CHR_1-XH}{|}}{CH}}$$

wherein

Y is the residue of a peptide alcohol,
$R_1$ is hydrogen or methyl, and
X is O or S, by solid phase technology, the improvement which comprises:

a) cleaving the amino protecting group A from a polymer resin containing an acetalyzed formylphenyl group of formula Vr

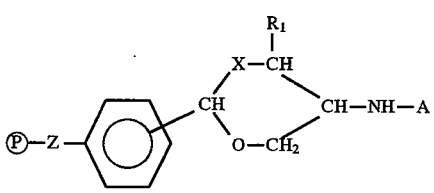

where

P is the residue of an insoluble synthetic polymer resin,
Z is a residue which joins the resin with the acetalyzed formylphenyl group, and $R_1$ and X are as defined above, wherein the acetalyzed formylphenyl group is m- or p- to Z;

and reacting the free amino group with the next N-protected amino acid by solid-phase technology until all of the amino acids corresponding to Y, as defined above, have been added to obtain a resin of formula Ir

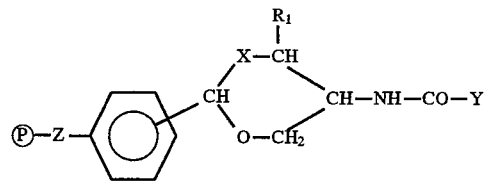

and b) hydrolyzing under acidic conditions the resin of formula Ir to obtain the peptide alcohol.

2. In a process for the production of a biologically active peptide alcohol of the formula $$Y-CO-NH-\underset{\underset{CH_2OH}{|}}{\overset{\overset{CHR_1-XH}{|}}{CH}}$$

wherein

Y is the residue of a peptide alcohol,
$R_1$ is hydrogen or methyl, and
X is O or S, by solid phase technology, the improvement which comprises:

a i) acetalyzing a resin of formula IIr

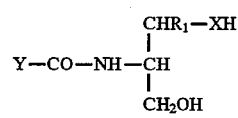

where

P is the residue of an insoluble synthetic polymer resin, and

Z is

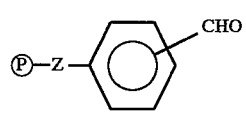

wherein $Q_1$ is the residue of a reactive group which is bonded to the polymer,
$Q_2$ is the residue of a reactive group which is bonded to the acetalyzed formylphenyl group,
D is a residue which joins the group $Q_1$ with the polymer,
E is a residue which joins the group $Q_2$ with the acetalized formylphenyl group, and
p and q, independently of one another, are 0 or 1, and the CHO group is m- or p- to Z, with an amino alcohol of the formula

where

A is an amino protecting group, and
$R_1$ and X are as defined above, to obtain a polymer resin containing an acetalyzed formylphenyl group of formula Vr

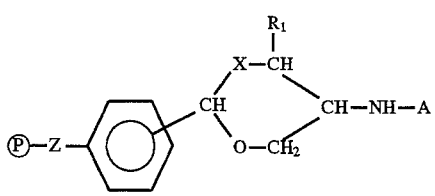

wherein P, Z, X, $R_1$ and A are as defined above, or a ii) acetalyzing a compound of the formula

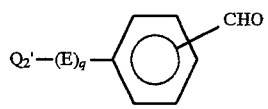

with an amino alcohol of the formula $HX—CHR_1—CH(NHA)—CH_2OH$ where X, A and $R_1$ are as defined above, to obtain a compound of formula VIr

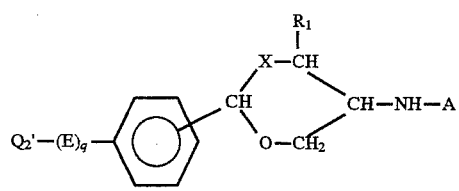

and reacting the compound of formula VIr with a resin of the formula

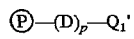

to obtain a polymer resin of formula Vr in which Z is $-(D)_p-Q_1-Q_2-(D)_q-$ where $Q_1'$ and $Q_2'$ are reactive groups which react together to form a $—Q_1-Q_2—$ bridge, and D, $Q_1$, $Q_2$, E, P, p and q are as defined above;

b) cleaving the protecting group A from the polymer resin of formula Vr and producing by solid-phase technology a resin of formula Ir

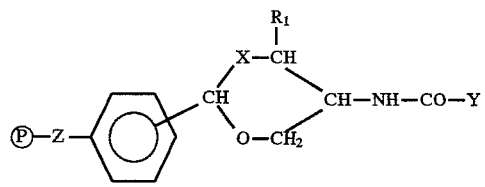

where P, Z, Y, $R_1$ and X are as defined above, and the acetalyzed formylphenyl group is m- or p- to Z; and c) hydrolyzing the resin of formula Ir under acidic conditions.

3. A process according to claim 2 in which Z is $-D-Q_1-Q_2-E-$ wherein

D and E are each independently alkylene of 1 to 5 carbon atoms or alkylenoxy of 1 to 5 carbon atoms, $Q_1$ is NH, and $Q_2$ is CO, or a residue of the formula $-CH_2-NH-CO-(CH_2)_5-NH-CO-CH-(O)_m-$
                                         $|$
                                         $R$ where R is hydrogen or methyl, and m is 0 or 1.

4. A process according to claim 2 in which P is polystyrene and Z is $—CH_2—NH—CO—CH(R)—(O)_m—$ and R is hydrogen or methyl.

5. A process according to claim 2 in which the acetalyzation in step a i) or step a ii) is carried out in the presence of an acid.

6. A process according to claim 2 in which the resin of formula Ir is prepared by a ii) reacting a compound of the formula

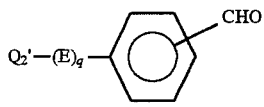

where $Q_2'$ is COOH,

E is alkylene of 1 to 5 carbon atoms or alkylenoxy of 1 to 5 carbon atoms, and q is 1, with an amino alcohol of the formula $HX—CHR_1—CH(NHA)—CH_2OH$ where A is an amino protecting group, to obtain a compound of formula VIr

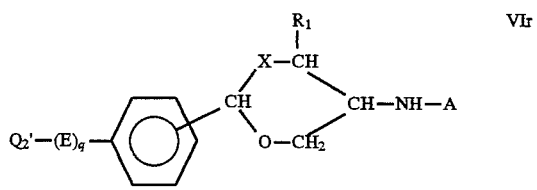

and reacting the compound of formula VIr with a resin of the formula

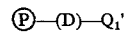

where

P is the residue of an insoluble synthetic polymer resin, $Q_1'$ is $NH_2$, and

D is alkylene of 1 to 5 carbon atoms, to obtain a compound of formula Vr in which Z is

-D-NH-CO-E-, b) cleaving the protecting group A from the compound of formula Vr and producing by solid-phase technology a resin of formula Ir.

7. A process according to claim 6 in which A is CO—$CF_3$, D is $CH_2$, E is $CH_2$—O, and P is polystyrene.

8. A process according to claim 2 in which Y is a residue of a somatostatin peptide alcohol or a biologically active peptide alcohol derivative or analog thereof.

9. A process according to claim 2 in which Y is a somatostatin peptide alcohol residue of the formula

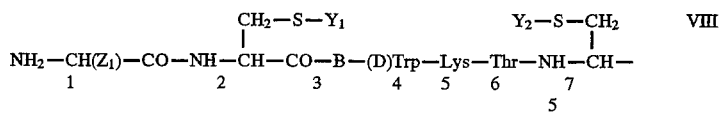
wherein
H$_2$N—CH(Z$_1$)—CO— is an (L)- or (D)-phenylalanine residue or an (L)- or (D)-tyrosine residue;
Y$_1$ and Y$_2$ together represent a direct bond; and
B is Phe or Tyr.
* * * * *

UNITED STATES PATENT AND TRADEMARK OFFICE
CERTIFICATE OF CORRECTION

PATENT NO. : 5,656,721
DATED : August 12, 1997
INVENTOR(S) : Rainer Albert, et al.

It is certified that error appears in the above-identified patent and that said Letters Patent is hereby corrected as shown below:

Title page, item [75], should read --Monika Mergler, Liestal; Walter Prikoszovich, Allschwil, both of Switzerland--.

Title page, item [19], should read --Mergler et al.--.

Signed and Sealed this

Sixth Day of January, 1998

Attest:

BRUCE LEHMAN

*Attesting Officer*         *Commissioner of Patents and Trademarks*